United States Patent
Colleran et al.

(10) Patent No.: US 8,025,681 B2
(45) Date of Patent: Sep. 27, 2011

(54) DYNAMIC MOTION SPINAL STABILIZATION SYSTEM

(75) Inventors: Dennis Colleran, North Attleboro, MA (US); Arnold Oyola, Northborough, MA (US); Michael Perriello, Hopedale, MA (US); Sally Carter, Northborough, MA (US); Joshua Morin, Attleboro, MA (US)

(73) Assignee: Theken Spine, LLC, Akron, OH (US)

( * ) Notice: Subject to any disclaimer, the term of this patent is extended or adjusted under 35 U.S.C. 154(b) by 618 days.

(21) Appl. No.: 11/693,394

(22) Filed: Mar. 29, 2007

(65) Prior Publication Data

US 2007/0233094 A1 Oct. 4, 2007

Related U.S. Application Data

(60) Provisional application No. 60/786,898, filed on Mar. 29, 2006, provisional application No. 60/831,879, filed on Jul. 19, 2006, provisional application No. 60/825,078, filed on Sep. 8, 2006, provisional application No. 60/826,807, filed on Sep. 25, 2006, provisional application No. 60/826,817, filed on Sep. 25, 2006.

(51) Int. Cl.
*A61B 17/70* (2006.01)

(52) U.S. Cl. ............. 606/257; 606/258; 606/259

(58) Field of Classification Search ......... 606/250–263, 606/264–279, 53, 54, 60, 246–249, 300–321; 623/17.11–17.16
See application file for complete search history.

(56) References Cited

U.S. PATENT DOCUMENTS

| | | | |
|---|---|---|---|
| 3,426,364 | A | 2/1969 | William |
| 3,807,394 | A | 4/1974 | Attenborough |
| 3,920,060 | A | 11/1975 | Heldmann et al. |
| 4,157,715 | A | 6/1979 | Westerhoff |
| 4,854,311 | A | 8/1989 | Steffee |
| 5,011,484 | A | 4/1991 | Breard |
| 5,019,080 | A | 5/1991 | Hemer |

(Continued)

FOREIGN PATENT DOCUMENTS

EP 0322334 6/1989

(Continued)

OTHER PUBLICATIONS

International Search Report issued for PCT/US2007/065525 dated Aug. 22, 2007.

(Continued)

*Primary Examiner* — Eduardo C Robert
*Assistant Examiner* — Christina Negrelli
(74) *Attorney, Agent, or Firm* — Middleton Reutlinger; Robert H. Eichenberger; Scott W. Higdon

(57) ABSTRACT

Provided is a system for dynamically stabilizing a spine. In one example, the system includes a first bone anchor coupled to a first polyaxial head and a second bone anchor coupled to a second polyaxial head. An axis passing through a center of each polyaxial head is aligned with a center of rotation. A first member has a first end movably coupled to the first polyaxial head and a second end. A second member has a third end coupled to the second polyaxial head and a fourth end moveably coupled to the second end. The first and second members are configured to maintain the alignment of the axes with the center of rotation during three dimensional movement of the first member relative to the second member.

23 Claims, 25 Drawing Sheets

U.S. PATENT DOCUMENTS

| | | |
|---|---|---|
| 5,053,036 A | 10/1991 | Perren et al. |
| 5,092,867 A | 3/1992 | Harms et al. |
| 5,129,899 A | 7/1992 | Small et al. |
| 5,129,900 A | 7/1992 | Asher et al. |
| 5,151,103 A | 9/1992 | Tepic et al. |
| 5,176,679 A | 1/1993 | Lin |
| 5,196,013 A | 3/1993 | Harms et al. |
| 5,196,014 A | 3/1993 | Lin |
| 5,257,994 A | 11/1993 | Lin |
| 5,261,909 A | 11/1993 | Sutterlin et al. |
| 5,300,073 A | 4/1994 | Ray et al. |
| 5,304,179 A | 4/1994 | Wagner |
| 5,312,404 A | 5/1994 | Asher et al. |
| 5,330,474 A | 7/1994 | Lin |
| 5,375,823 A | 12/1994 | Navas et al. |
| 5,380,324 A | 1/1995 | Muller et al. |
| 5,403,314 A | 4/1995 | Currier |
| 5,413,576 A | 5/1995 | Rivard |
| 5,413,602 A | 5/1995 | Metz-Stavenhagen |
| 5,415,661 A | 5/1995 | Holmes et al. |
| 5,423,816 A | 6/1995 | Lin |
| 5,435,680 A | 7/1995 | Schuster |
| 5,474,551 A | 12/1995 | Finn et al. |
| 5,474,553 A | 12/1995 | Baumgart |
| 5,476,463 A | 12/1995 | Boachie et al. |
| 5,480,401 A | 1/1996 | Navas |
| 5,487,744 A | 1/1996 | Howland |
| 5,496,318 A | 3/1996 | Howland et al. |
| 5,498,262 A | 3/1996 | Bryan |
| 5,498,263 A | 3/1996 | DiNelio et al. |
| 5,501,684 A | 3/1996 | Schlapfer |
| 5,520,688 A | 5/1996 | Lin |
| 5,540,687 A | 7/1996 | Fairley et al. |
| 5,540,688 A | 7/1996 | Navas et al. |
| 5,540,690 A | 7/1996 | Miller et al. |
| 5,562,660 A | 10/1996 | Grob |
| 5,562,661 A | 10/1996 | Yoshimi et al. |
| 5,562,662 A | 10/1996 | Brumfield et al. |
| 5,569,248 A | 10/1996 | Mathews |
| 5,575,791 A | 11/1996 | Lin |
| 5,582,612 A | 12/1996 | Lin |
| 5,584,833 A | 12/1996 | Fournet-Fayard et al. |
| 5,584,887 A | 12/1996 | Kambin |
| 5,591,165 A | 1/1997 | Jackson |
| 5,591,166 A | 1/1997 | Bernhardt et al. |
| 5,603,713 A | 2/1997 | Aust et al. |
| 5,609,592 A | 3/1997 | Brumfield |
| 5,611,800 A | 3/1997 | Davis et al. |
| 5,613,968 A | 3/1997 | Lin |
| 5,620,443 A | 4/1997 | Gertzbein et al. |
| 5,628,740 A | 5/1997 | Mullane |
| 5,643,264 A | 7/1997 | Sherman et al. |
| 5,672,175 A | 9/1997 | Martin et al. |
| 5,681,313 A | 10/1997 | Diez |
| 5,688,275 A | 11/1997 | Koros et al. |
| 5,704,936 A | 1/1998 | Mazel |
| 5,716,357 A | 2/1998 | Rogozinski |
| 5,725,528 A | 3/1998 | Errico et al. |
| 5,725,582 A | 3/1998 | Bevan et al. |
| 5,733,284 A | 3/1998 | Martin |
| 5,735,851 A | 4/1998 | Errico et al. |
| 5,735,853 A | 4/1998 | Olerud |
| 5,741,255 A | 4/1998 | Kraq et al. |
| 5,800,435 A | 9/1998 | Errico et al. |
| 5,827,286 A | 10/1998 | Incavo et al. |
| 5,836,948 A | 11/1998 | Zucherman et al. |
| 5,846,245 A | 12/1998 | McCarthy et al. |
| 5,855,580 A | 1/1999 | Kreidler et al. |
| 5,860,977 A | 1/1999 | Zucherman et al. |
| 5,876,404 A | 3/1999 | Zucherman et al. |
| 5,879,350 A | 3/1999 | Sherman et al. |
| 5,891,145 A | 4/1999 | Morrison et al. |
| 5,899,902 A | 5/1999 | Brown et al. |
| 5,902,303 A | 5/1999 | Ecljpf et al. |
| 5,902,304 A | 5/1999 | Walker et al. |
| 5,944,719 A | 8/1999 | Leban |
| 5,951,553 A | 9/1999 | Betz et al. |
| 5,951,555 A | 9/1999 | Rehak et al. |
| 5,954,722 A | 9/1999 | Bono |
| 5,961,516 A | 10/1999 | Graf |
| 5,964,763 A | 10/1999 | Incavo et al. |
| 5,976,135 A | 11/1999 | Sherman et al. |
| 5,984,924 A | 11/1999 | Asher et al. |
| 5,993,449 A | 11/1999 | Schlapfer et al. |
| 6,017,345 A | 1/2000 | Richelsoph |
| 6,019,769 A | 2/2000 | McCarthy et al. |
| 6,030,388 A | 2/2000 | Yoshimi et al. |
| 6,039,738 A | 3/2000 | Sanders et al. |
| 6,045,552 A | 4/2000 | Zucherman et al. |
| 6,048,342 A | 4/2000 | Zucherman et al. |
| 6,050,997 A | 4/2000 | Mullane |
| 6,063,090 A | 5/2000 | Schlapfer |
| 6,068,630 A | 5/2000 | Zucherman et al. |
| 6,074,390 A | 6/2000 | Zucherman et al. |
| 6,077,262 A | 6/2000 | Schlapfer et al. |
| 6,080,156 A | 6/2000 | Asher et al. |
| 6,083,224 A | 7/2000 | Gertzbein et al. |
| 6,090,112 A | 7/2000 | Zucherman et al. |
| 6,146,383 A | 11/2000 | Studer et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,183,471 B1 | 2/2001 | Zucherman et al. |
| 6,187,005 B1 | 2/2001 | Brace et al. |
| 6,190,387 B1 | 2/2001 | Zucherman et al. |
| 6,231,575 B1 | 5/2001 | Krag |
| 6,235,030 B1 | 5/2001 | Zucherman et al. |
| 6,235,033 B1 | 5/2001 | Brace et al. |
| 6,235,059 B1 | 5/2001 | Benezech |
| 6,238,396 B1 | 5/2001 | Lomardo |
| 6,238,397 B1 | 5/2001 | Zucherman et al. |
| 6,241,730 B1 | 6/2001 | Betz et al. |
| 6,241,731 B1 | 6/2001 | Fiz |
| 6,261,288 B1 | 7/2001 | Jackson |
| 6,267,764 B1 | 7/2001 | Elberg |
| 6,267,765 B1 | 7/2001 | Taylor et al. |
| 6,273,889 B1 | 8/2001 | Richelsoph |
| 6,280,444 B1 | 8/2001 | Zucherman et al. |
| 6,280,445 B1 | 8/2001 | Morrison et al. |
| 6,287,308 B1 | 9/2001 | Betz et al. |
| 6,296,644 B1 | 10/2001 | Saurat et al. |
| 6,309,391 B1 | 10/2001 | Crandall et al. |
| 6,315,779 B1 | 11/2001 | Morrison et al. |
| 6,331,179 B1 | 12/2001 | Freid et al. |
| 6,332,882 B1 | 12/2001 | Zucherman et al. |
| 6,332,883 B1 | 12/2001 | Zucherman et al. |
| 6,355,038 B1 | 3/2002 | Pisharodi |
| 6,413,257 B1 | 7/2002 | Lin et al. |
| 6,419,676 B1 | 7/2002 | Zucherman et al. |
| 6,419,677 B2 | 7/2002 | Zucherman et al. |
| 6,423,069 B1 | 7/2002 | Sellers |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,454,769 B2 | 9/2002 | Wagner et al. |
| 6,471,706 B1 | 10/2002 | Schumacher et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,520,990 B1 | 2/2003 | Ray |
| 6,529,889 B1 | 3/2003 | Bromberq et al. |
| 6,554,831 B1 | 4/2003 | Rivard et al. |
| 6,575,975 B2 | 6/2003 | Brace et al. |
| 6,582,433 B2 | 6/2003 | Yun |
| 6,585,738 B1 | 7/2003 | Mangione et al. |
| 6,610,062 B2 | 8/2003 | Bailey et al. |
| 6,623,485 B2 | 9/2003 | Doubler et al. |
| 6,626,904 B1 | 9/2003 | Jammet et al. |
| 6,626,909 B2 | 9/2003 | Chin |
| 6,641,583 B2 | 11/2003 | Shluzas et al. |
| 6,645,207 B2 | 11/2003 | Dixon et al. |
| 6,652,527 B2 | 11/2003 | Zucherman et al. |
| 6,652,534 B2 | 11/2003 | Zucherman et al. |
| 6,663,632 B1 | 12/2003 | Frigg |
| 6,669,697 B1 | 12/2003 | Pisharodi |
| 6,673,074 B2 | 1/2004 | Shluzas |
| 6,679,883 B2 | 1/2004 | Hawkes et al. |

| | | |
|---|---|---|
| 6,685,705 B1 | 2/2004 | Taylor |
| 6,689,133 B2 | 2/2004 | Morrison et al. |
| 6,695,842 B2 | 2/2004 | Zucherman et al. |
| 6,699,246 B2 | 3/2004 | Zucherman et al. |
| 6,709,433 B1 | 3/2004 | Schoenefeld |
| 6,743,257 B2 | 6/2004 | Castro |
| 6,755,830 B2 | 6/2004 | Minfelde |
| 6,761,720 B1 | 7/2004 | Senegas |
| 6,802,844 B2 | 10/2004 | Ferree |
| 6,811,567 B2 | 11/2004 | Reiley |
| 6,835,205 B2 | 12/2004 | Atkinson et al. |
| 6,852,113 B2 | 2/2005 | Nathanson et al. |
| 6,858,031 B2 | 2/2005 | Morrison et al. |
| 6,884,243 B2 | 4/2005 | Sellers |
| 6,887,242 B2 | 5/2005 | Doubler et al. |
| 6,890,334 B2 | 5/2005 | Brace et al. |
| 6,902,566 B2 | 6/2005 | Zucherman et al. |
| 6,945,972 B2 | 9/2005 | Frigg et al. |
| 6,945,974 B2 | 9/2005 | Dalton |
| 6,945,975 B2 | 9/2005 | Dalton |
| 6,964,664 B2 | 11/2005 | Freid et al. |
| 6,964,666 B2 | 11/2005 | Jackson |
| 6,966,910 B2 | 11/2005 | Ritland |
| 6,972,020 B1 | 12/2005 | Grayson et al. |
| 6,974,460 B2 | 12/2005 | Carbone et al. |
| 6,979,334 B2 | 12/2005 | Dalton |
| 6,986,771 B2 | 1/2006 | Paul |
| 6,989,011 B2 | 1/2006 | Paul |
| 6,991,632 B2 | 1/2006 | Ritland |
| 7,001,389 B1 | 2/2006 | Navarro et al. |
| RE39,035 E | 3/2006 | Finn et al. |
| 7,011,685 B2 | 3/2006 | Arnin et al. |
| 7,029,473 B2 | 4/2006 | Zucherman et al. |
| 7,029,475 B2 | 4/2006 | Panjabi |
| 7,041,136 B2 | 5/2006 | Goble et al. |
| 7,048,736 B2 | 5/2006 | Robinson et al. |
| 7,060,066 B2 | 6/2006 | Zhao et al. |
| 7,074,237 B2 | 7/2006 | Goble et al. |
| 7,083,621 B2 | 8/2006 | Shaolian et al. |
| 7,135,021 B2 | 11/2006 | Lin |
| 7,163,539 B2 | 1/2007 | Abdelgany |
| 7,182,782 B2 | 2/2007 | Kirschman |
| 7,186,255 B2 | 3/2007 | Baynham et al. |
| 7,195,632 B2 | 3/2007 | Biedermann et al. |
| 7,195,633 B2 | 3/2007 | Medoff et al. |
| 7,201,751 B2 | 4/2007 | Zucherman et al. |
| 7,204,837 B2 | 4/2007 | Paul |
| 7,207,992 B2 | 4/2007 | Ritland |
| 7,214,227 B2 | 5/2007 | Colleran et al. |
| 7,291,150 B2 | 11/2007 | Graf |
| 2001/0021851 A1 | 9/2001 | Eberlein et al. |
| 2002/0058939 A1 | 5/2002 | Wagner et al. |
| 2002/0095154 A1 | 7/2002 | Atkinson et al. |
| 2002/0133155 A1 | 9/2002 | Ferree |
| 2002/0151978 A1 | 10/2002 | Zacouto et al. |
| 2003/0009226 A1 | 1/2003 | Graf |
| 2003/0028191 A1 | 2/2003 | Shluzas |
| 2003/0100904 A1 | 5/2003 | Biedermann |
| 2003/0105462 A1 | 6/2003 | Haider |
| 2003/0109880 A1 | 6/2003 | Shirado et al. |
| 2003/0125741 A1 | 7/2003 | Biedermann et al. |
| 2003/0153912 A1 | 8/2003 | Graf |
| 2003/0171749 A1 | 9/2003 | Le Couedic et al. |
| 2003/0220643 A1 | 11/2003 | Sret |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0049280 A1 | 3/2004 | Cauthen |
| 2004/0068319 A1 | 4/2004 | Cordaro |
| 2004/0073215 A1 | 4/2004 | Carli |
| 2004/0078040 A1 | 4/2004 | Feijtel |
| 2004/0092930 A1 | 5/2004 | Petit et al. |
| 2004/0116927 A1 | 6/2004 | Graf |
| 2004/0127897 A1 | 7/2004 | Freid et al. |
| 2004/0143264 A1 | 7/2004 | McAfee |
| 2004/0147928 A1* | 7/2004 | Landry et al. .................. 606/61 |
| 2004/0153159 A1 | 8/2004 | Cauthen |
| 2004/0181223 A1 | 9/2004 | Ritland |
| 2004/0186591 A1 | 9/2004 | Lang |
| 2004/0220570 A1 | 11/2004 | Frigg |
| 2004/0220668 A1 | 11/2004 | Eisermann et al. |
| 2004/0225289 A1 | 11/2004 | Biedermann et al. |
| 2005/0004573 A1 | 1/2005 | Abdou |
| 2005/0004574 A1 | 1/2005 | Muckter |
| 2005/0010214 A1 | 1/2005 | Tassin |
| 2005/0033298 A1 | 2/2005 | Hawker et al. |
| 2005/0033432 A1 | 2/2005 | Gordon et al. |
| 2005/0049708 A1 | 3/2005 | Atkinson et al. |
| 2005/0070899 A1 | 3/2005 | Doubler et al. |
| 2005/0070901 A1 | 3/2005 | David |
| 2005/0085813 A1 | 4/2005 | Spitler et al. |
| 2005/0085814 A1 | 4/2005 | Sherman et al. |
| 2005/0085815 A1 | 4/2005 | Harms et al. |
| 2005/0090823 A1 | 4/2005 | Bartimus |
| 2005/0113927 A1 | 5/2005 | Malek |
| 2005/0119748 A1 | 6/2005 | Reiley et al. |
| 2005/0125063 A1 | 6/2005 | Matge et al. |
| 2005/0131404 A1 | 6/2005 | Mazda et al. |
| 2005/0131405 A1 | 6/2005 | Molz et al. |
| 2005/0131406 A1 | 6/2005 | Reileyet al. |
| 2005/0131407 A1 | 6/2005 | Sievol et al. |
| 2005/0137594 A1 | 6/2005 | Doubler et al. |
| 2005/0143737 A1 | 6/2005 | Pafford et al. |
| 2005/0143742 A1 | 6/2005 | Porcher |
| 2005/0143823 A1 | 6/2005 | Boyd et al. |
| 2005/0149023 A1 | 7/2005 | Ritland |
| 2005/0165398 A1 | 7/2005 | Reiley |
| 2005/0171540 A1 | 8/2005 | Lim et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182400 A1 | 8/2005 | White |
| 2005/0182401 A1* | 8/2005 | Timm et al. ................. 606/61 |
| 2005/0182409 A1 | 8/2005 | Callahan et al. |
| 2005/0192571 A1 | 9/2005 | Abdelgany |
| 2005/0203517 A1 | 9/2005 | Jahng et al. |
| 2005/0203519 A1 | 9/2005 | Harms et al. |
| 2005/0209594 A1 | 9/2005 | Sellers |
| 2005/0216005 A1 | 9/2005 | Howland |
| 2005/0222569 A1 | 10/2005 | Panjabi |
| 2005/0228386 A1 | 10/2005 | Ziolo et al. |
| 2005/0245929 A1 | 11/2005 | Winslow |
| 2005/0245930 A1 | 11/2005 | Timm et al. |
| 2005/0256578 A1 | 11/2005 | Blatt et al. |
| 2005/0261682 A1 | 11/2005 | Ferree |
| 2005/0261770 A1 | 11/2005 | Kuiper et al. |
| 2005/0267470 A1 | 12/2005 | McBride |
| 2005/0267474 A1 | 12/2005 | Dalton |
| 2005/0278026 A1 | 12/2005 | Gordon et al. |
| 2005/0283244 A1 | 12/2005 | Gordon et al. |
| 2005/0288670 A1 | 12/2005 | Panjabi et al. |
| 2006/0009767 A1 | 1/2006 | Kiester |
| 2006/0015100 A1 | 1/2006 | Panjabi et al. |
| 2006/0015104 A1 | 1/2006 | Dalton |
| 2006/0036240 A1 | 2/2006 | Colleran et al. |
| 2006/0052783 A1 | 3/2006 | Dant et al. |
| 2006/0052786 A1 | 3/2006 | Dant et al. |
| 2006/0058787 A1 | 3/2006 | Stryker |
| 2006/0079899 A1 | 4/2006 | Ritland |
| 2006/0084984 A1 | 4/2006 | Kim |
| 2006/0084987 A1 | 4/2006 | Krishna et al. |
| 2006/0085076 A1 | 4/2006 | Krishna et al. |
| 2006/0089717 A1 | 4/2006 | Krishna et al. |
| 2006/0106382 A1 | 5/2006 | Gournay et al. |
| 2006/0142758 A1 | 6/2006 | Petit |
| 2006/0149229 A1 | 7/2006 | Kwak et al. |
| 2006/0149256 A1 | 7/2006 | Wagner et al. |
| 2006/0155279 A1 | 7/2006 | Ogilvie |
| 2006/0189983 A1 | 8/2006 | Fallin et al. |
| 2006/0189984 A1* | 8/2006 | Fallin et al. .................. 606/61 |
| 2006/0190090 A1 | 8/2006 | Plaskon et al. |
| 2006/0229608 A1 | 10/2006 | Foster et al. |
| 2006/0229613 A1 | 10/2006 | Timm et al. |
| 2006/0235399 A1 | 10/2006 | Carls et al. |
| 2006/0235518 A1 | 10/2006 | Blain |

| | | | |
|---|---|---|---|
| 2006/0241612 A1 | 10/2006 | Robert et al. | |
| 2006/0241769 A1 | 10/2006 | Gordon et al. | |
| 2006/0241771 A1 | 10/2006 | Gordon et al. | |
| 2006/0247635 A1 | 11/2006 | Gordon et al. | |
| 2006/0247779 A1 | 11/2006 | Gordon et al. | |
| 2006/0265074 A1 | 11/2006 | Krishna et al. | |
| 2006/0271046 A1 | 11/2006 | Kwak et al. | |
| 2006/0282080 A1 | 12/2006 | Albert et al. | |
| 2006/0293663 A1 | 12/2006 | Walkenhorst et al. | |
| 2007/0016193 A1 | 1/2007 | Ritland | |
| 2007/0032123 A1 | 2/2007 | Timm et al. | |
| 2007/0043356 A1 | 2/2007 | Timm et al. | |
| 2007/0050631 A1 | 3/2007 | Shimizu et al. | |
| 2007/0055247 A1 | 3/2007 | Jahng | |

FOREIGN PATENT DOCUMENTS

| | | |
|---|---|---|
| EP | 0669109 | 5/1999 |
| EP | 1072228 | 1/2001 |
| EP | 1072228 A | 1/2001 |
| WO | WO 2006/020530 A | 2/2006 |
| WO | WO2006020530 | 2/2006 |

OTHER PUBLICATIONS

PCT/US2007/065525, International Search Report, European Patent Office, Aug. 22, 2007.

European Patent Office, International Search Report and Written Opinion, Report, Aug. 3, 2006, pp. 1-19, PCT/US2005/027996, European Patent Office, Riswijk, the Netherlands.

European Patent Office, International Search Report and Written Opinion, Report, May 10, 2006, pp. 1-18, PCT/US2005/036339, European Patent Office, Rijswijk, the Netherlands.

European Patent Office, International Search Report and Written Opinion, Report, Aug. 22, 2007, pp. 1-16, PCT/US2004/035000, European Patent Office, Riswijk, the Netherlands.

* cited by examiner

DYNAMIC MOTION SPINAL STABILIZATION SYSTEM

CLAIM OF PRIORITY

This application claims priority from U.S. Provisional Patent Application Ser. No. 60/786,898, filed on Mar. 29, 2006, U.S. Provisional Patent Application Ser. No. 60/831,879, filed on Jul. 19, 2006, U.S. Provisional Patent Application Ser. No. 60/825,078, filed on Sep. 8, 2006, U.S. Provisional Patent Application Ser. No. 60/826,807, filed on Sep. 25, 2006, and U.S. Provisional Patent Application Ser. No. 60/826,817, filed on Sep. 25, 2006, all of which are incorporated by reference herein in their entirety.

FIELD OF THE INVENTION

This disclosure relates to skeletal stabilization and, more particularly, to systems and method for stabilization of human spines and, even more particularly, to dynamic stabilization techniques.

BACKGROUND

The human spine is a complex structure designed to achieve a myriad of tasks, many of them of a complex kinematic nature. The spinal vertebrae allow the spine to flex in three axes of movement relative to the portion of the spine in motion. These axes include the horizontal (bending either forward/anterior or aft/posterior), roll (bending to either left or right side) and vertical (twisting of the shoulders relative to the pelvis).

In flexing about the horizontal axis into flexion (bending forward or anterior) and extension (bending backward or posterior), vertebrae of the spine must rotate about the horizontal axis to various degrees of rotation. The sum of all such movement about the horizontal axis produces the overall flexion or extension of the spine. For example, the vertebrae that make up the lumbar region of the human spine move through roughly an arc of 15° relative to its adjacent or neighboring vertebrae. Vertebrae of other regions of the human spine (e.g., the thoracic and cervical regions) have different ranges of movement. Thus, if one were to view the posterior edge of a healthy vertebrae, one would observe that the edge moves through an arc of some degree (e.g., of about 15° in flexion and about 5° in extension if in the lumbar region) centered about a center of rotation. During such rotation, the anterior (front) edges of neighboring vertebrae move closer together, while the posterior edges move farther apart, compressing the anterior of the spine. Similarly, during extension, the posterior edges of neighboring vertebrae move closer together while the anterior edges move farther apart thereby compressing the posterior of the spine. During flexion and extension, the vertebrae move in horizontal relationship to each other providing up to 2-3 mm of translation.

In a normal spine, the vertebrae also permit right and left lateral bending. Accordingly, right lateral bending indicates the ability of the spine to bend over to the right by compressing the right portions of the spine and reducing the spacing between the right edges of associated vertebrae. Similarly, left lateral bending indicates the ability of the spine to bend over to the left by compressing the left portions of the spine and reducing the spacing between the left edges of associated vertebrae. The side of the spine opposite that portion compressed is expanded, increasing the spacing between the edges of vertebrae comprising that portion of the spine. For example, the vertebrae that make up the lumbar region of the human spine rotate about an axis of roll, moving through an arc of around 100 relative to its neighbor vertebrae throughout right and left lateral bending.

Rotational movement about a vertical axis relative is also natural in the healthy spine. For example, rotational movement can be described as the clockwise or counter-clockwise twisting rotation of the vertebrae during a golf swing.

In a healthy spine, the inter-vertebral spacing between neighboring vertebrae is maintained by a compressible and somewhat elastic disc. The disc serves to allow the spine to move about the various axes of rotation and through the various arcs and movements required for normal mobility. The elasticity of the disc maintains spacing between the vertebrae during flexion and lateral bending of the spine thereby allowing room or clearance for compression of neighboring vertebrae. In addition, the disc allows relative rotation about the vertical axis of neighboring vertebrae allowing twisting of the shoulders relative to the hips and pelvis. A healthy disc further maintains clearance between neighboring vertebrae thereby enabling nerves from the spinal chord to extend out of the spine between neighboring vertebrae without being squeezed or impinged by the vertebrae.

In situations where a disc is not functioning properly, the inter-vertebral disc tends to compress thereby reducing inter-vertebral spacing and exerting pressure on nerves extending from the spinal cord. Various other types of nerve problems may be experienced in the spine, such as exiting nerve root compression in the neural foramen, passing nerve root compression, and enervated annulus (where nerves grow into a cracked/compromised annulus, causing pain every time the disc/annulus is compressed), as examples. Many medical procedures have been devised to alleviate such nerve compression and the pain that results from nerve pressure. Many of these procedures revolve around attempts to prevent the vertebrae from moving too close to each in order to maintain space for the nerves to exit without being impinged upon by movements of the spine.

In one such procedure, screws are embedded in adjacent vertebrae pedicles and rigid rods or plates are then secured between the screws. In such a situation, the pedicle screws press against the rigid spacer which serves to distract the degenerated disc space thereby maintaining adequate separation between the neighboring vertebrae to prevent the vertebrae from compressing the nerves. Although the foregoing procedure prevents nerve pressure due to extension of the spine, when the patient then tries to bend forward (putting the spine in flexion), the posterior portions of at least two vertebrae are effectively held together. Furthermore, the lateral bending or rotational movement between the affected vertebrae is significantly reduced, due to the rigid connection of the spacers. Overall movement of the spine is reduced as more vertebras are distracted by such rigid spacers. This type of spacer not only limits the patient's movements, but also places additional stress on other portions of the spine, such as adjacent vertebrae without spacers, often leading to further complications at a later date.

In other procedures, dynamic fixation devices are used. However, conventional dynamic fixation devices do not facilitate lateral bending and rotational movement with respect to the fixated discs. This can cause further pressure on the neighboring discs during these types of movements, which over time may cause additional problems in the neighboring discs.

Accordingly, dynamic systems which approximate and enable a fuller range of motion while providing stabilization of a spine are needed.

SUMMARY

In one embodiment, a dynamic stabilization system is provided with a first bone anchor coupled to a first polyaxial head and a second bone anchor coupled to a second polyaxial head, wherein a first axis passing through a center of the first polyaxial head is aligned with a center of rotation and a second axis passing through a center of the second polyaxial head is aligned with the center of rotation. A first member has a first end movably coupled to the first polyaxial head and a second end. A second member has a third end coupled to the second polyaxial head and a fourth end moveably coupled to the second end. The first and second members are configured to maintain the alignment of the first and second axes with the center of rotation during three dimensional movement of the first member relative to the second member.

In another embodiment, a dynamic stabilization device is provided with a first member having first and second ends, wherein the first end is configured to movably couple to a first polyaxial head and includes a first axis that extends through the first end and intersects a center point. A second member has a third end configured to couple to a second polyaxial head, wherein the third end includes a second axis that extends through the third end and intersects the center point, and a fourth end moveably coupled to the second end. A third member movably couples the second and fourth ends, wherein the first, second, and third members are configured to maintain the intersection of the first and second axes with the center point as the center point moves along a curved three dimensional surface during movement of the first member relative to the second member.

In yet another embodiment, a method provides identifying a center of rotation between first and second vertebrae, coupling a first member of a dynamic stabilization device to a first polyaxial head, and coupling a second member of the dynamic stabilization device to a second polyaxial head. The method also provides orienting an axis of the first polyaxial head with the center of rotation, orienting an axis of the second polyaxial head with the center of rotation, and securing the first and second members relative to the first and second polyaxial heads, respectively, to maintain the orientation of the first and second axes with the center of rotation.

BRIEF DESCRIPTION OF THE DRAWINGS

For a more complete understanding of the present invention and the advantages thereof, reference is now made to the following Detailed Description taken in conjunction with the accompanying drawings, in which.

DETAILED DESCRIPTION

Figure 1:
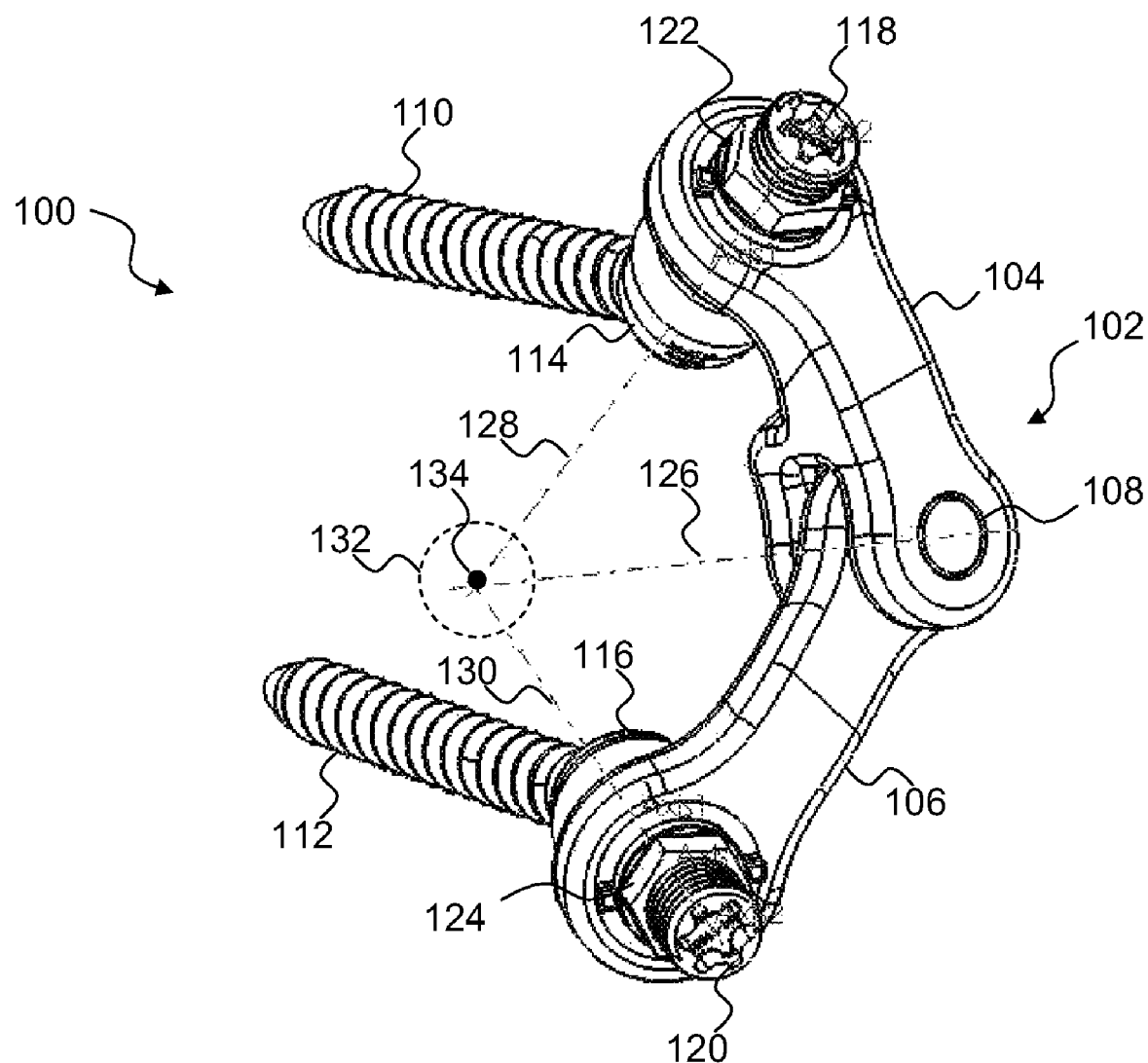
FIG. 1 is a perspective view of an embodiment of a dynamic stabilization system.

It is to be understood that the following disclosure provides many different embodiments, or examples, for implementing different features of the disclosure. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Certain aspects of the present disclosure provide dynamic stabilization systems, dynamic stabilization devices, and/or methods for maintaining spacing between consecutive neighboring vertebrae and stabilizing a spine, while allowing movement of the vertebrae relative to each other in at least two and preferably three axes of rotation. The neighboring vertebrae may be immediately next to each other or spaced from each other by one or more intervening vertebrae.

It is sometimes difficult to match a dynamic stabilization system with a particular patient's anatomical structure while ensuring that a minimum range of motion is available for the dynamic implant due to factors such as the variability of pedicle to pedicle distance in the lumbar spine. Generally, it may be desirable to have a dynamic stabilization system implanted at a neutral position that allows for a minimum available range of motion, while having the system aligned with a center of rotation that is placed, for example, at the 60-70% A-P marker of a vertebral body.

For instance, if a sliding dynamic stabilization system has to be extended to reach amply spaced pedicles, the system may not have sufficient engagement left for flexion (i.e., the system may reach the end of the sliding motion before full flexion is achieved). In order to have a predictable and consistent range of motion, it may be desirable to have the relative starting engagement always be the same (e.g., neutral). This may also be desirable to ensure that dampening forces are consistent at both extremes of relative motion.

One possible solution to address the fit of a dynamic stabilization system to variations in anatomy is to design multiple sizes. For example, such dynamic stabilization systems may have a fixed relative starting engagement so the full range of motion would be available. However, the location of the center of rotation might need to be shifted forward or backwards in the A-P direction to fit the dynamic stabilization system (in its neutral engagement) in the anatomy. A sensitivity study has shown that a small change in pedicle to pedicle distance (e.g., one mm) may shift the center of rotation from the 65% A-P mark to the 70% A-P mark (i.e., a 5% change). A further change of pedicle to pedicle distance by another one millimeter may place the center of rotation at the 75% A-P mark, which may not be acceptable. As such, multiple sizes with overlapping ranges would have to be designed to accommodate all anatomy variations, align the center of rotation to the 60-70% A-P mark, and enable co-alignment of a dynamic stabilization system pair (i.e., left and right sides).

Accordingly, the following disclosure describes dynamic stabilization systems, devices, and methods for dynamic stabilization which may provide for adjustable distraction of the inter-vertebral space while still allowing a patient a substantial range of motion in two and/or three dimensions. Such a dynamic stabilization system may allow the vertebrae to which it is attached to move through a natural arc that may resemble an imaginary three dimensional surface such as a sphere or an ellipsoid. Accordingly, such a system may aid in permitting a substantial range of motion in flexion, extension, rotation, anterior-posterior translation and/or other desired types of natural spinal motion.

Referring to FIG. 1, one embodiment of a spine stabilization system 100 is illustrated. The spine stabilization system 100 may include a dynamic stabilization device 102 that includes two members 104 and 106 coupled by a pin 108. The pin 108 may enable the two members 104 and 106 to move with respect to one another, as will be described later in greater detail.

Each member 104 and 106 may be secured to a portion of a spine (not shown), such as a pedicle, by a fastening element such as a bone anchor (e.g., a pedicle screw) 110 and 112, respectively. Each bone anchor 110 and 112 may include or be attached to a polyaxial head, 114 and 116, respectively. The member 104 may be coupled to the polyaxial head 114 of its respective bone anchor 110 using, for example, a bearing post 118 (e.g., a set screw) and a locking nut 122. Similarly, the member 106 may be coupled to the polyaxial head 116 of its respective bone anchor 112 using, for example, a bearing post 120 (e.g., a set screw) and a locking nut 124.

As illustrated in FIG. 1, the pin 108 may be aligned with a first axis 126. The bearing posts 118 and 120 may be aligned with a second axis 128 and a third axis 130, respectively. The axes 126, 128, and 130 may intersect at area 132 (e.g., an area of rotation). In some embodiments, the axes 126, 128, and 130 may intersect at a point 134 (e.g., a center of rotation) within the area 132. The point 134 may be stationary or may move within the area 132 in conjunction with movement of the vertebrae (not shown in FIG. 1) to which the spinal stabilization device 102 is coupled. It is understood that the area 132 and the point 134 are for purposes of illustration only and are not limited to the shapes or sizes shown. For example, while the area 132 is shown as a sphere, the area may be an ellipsoid or other shape. Furthermore, while the axes 126, 128, and 130 are shown intersecting each other at the point 134, it is understood that they may not actually intersect one another, but may instead pass within a certain distance of each other. Furthermore, the point 134 need not be a stationary point, but may follow a path on or through the area 132. For example, the point 134 may move along a surface of the area 132 such that the area 132 provides a shell, and movement of the point 134 is constrained by the device 102 to an outer surface of the shell. For purposes of convenience, the term center of rotation may be used herein to refer to a specific point and/or a three dimensional surface.

Figure 2:
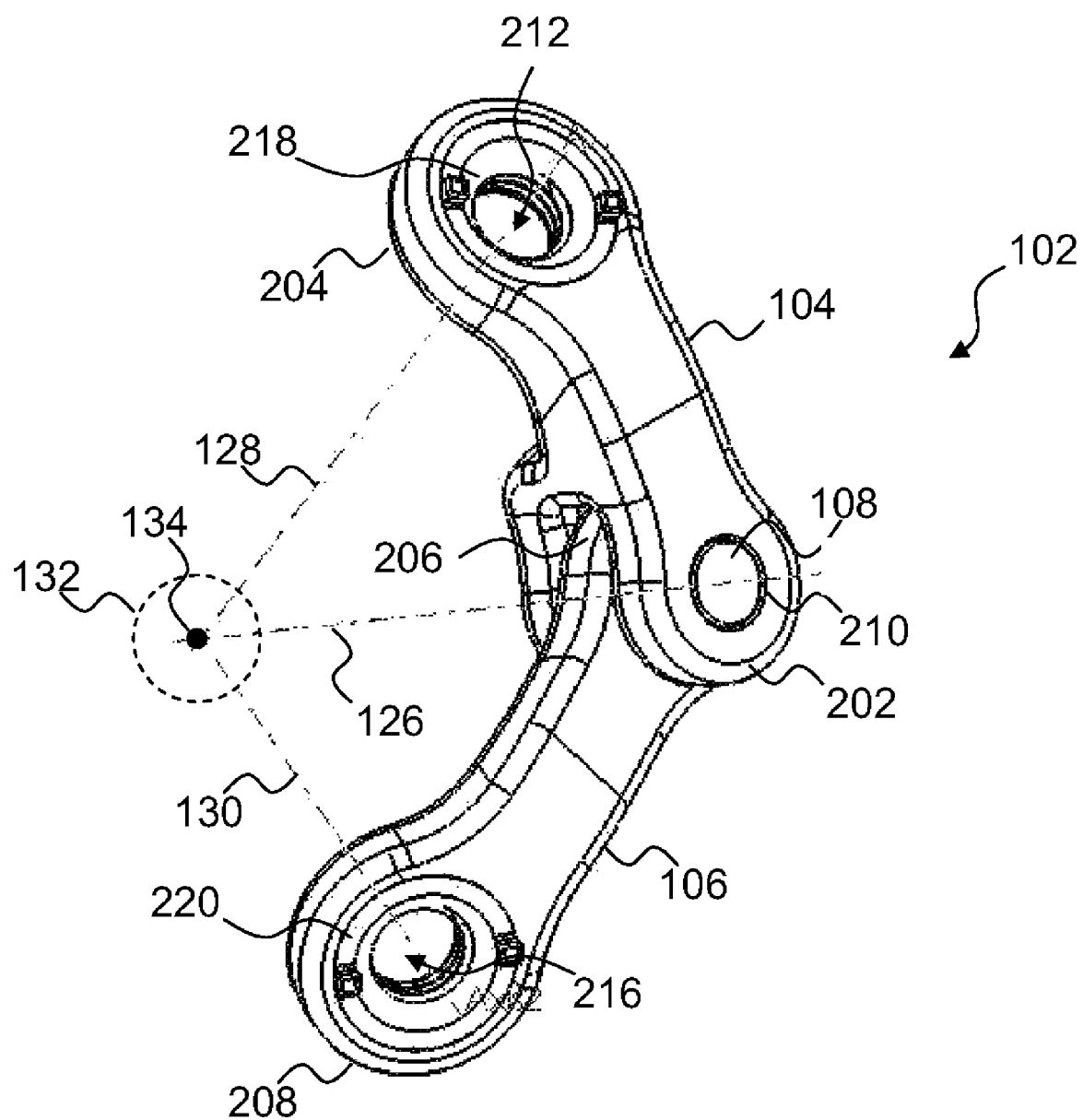
FIG. 2 is a perspective view of one embodiment of a brace that may be used in the dynamic stabilization system of FIG. 1.

Referring to FIG. 2, one embodiment of the dynamic stabilization device 102 is illustrated. As stated with respect to FIG. 1, the dynamic stabilization device 102 may include two members 104 and 106 that are coupled via the pin 108. In the present example, the member 104 may include a joint end 202 and a fastening end 204, and the member 106 may include a joint end 206 and a fastening end 208. The joint end 202 of the member 104 may include one or more apertures 210 and the fastening end 204 of the member 104 may include an aperture 212. Similarly, the joint end 206 of the member 106 may include an aperture 214 (shown in FIG. 6) and the fastening end 208 of the member 106 may include an aperture 216. The pin 108 may couple the members 104 and 106 via insertion into the apertures 210 and 214, respectively. The bearing posts 118 and 120 (shown in FIG. 1) may be inserted into apertures 212 and 216, respectively, to couple members 104 and 106 to pedicles or other bone (not shown in FIG. 2).

In the present embodiment, one or more of the apertures 210, 212, 214, and 216 may contain a bushing or other insertion member 218. For example, as illustrated, the aperture 212 may include a bushing 218 and the aperture 216 may include a bushing 220. The bushings 218 and 220 may aid in securing the dynamic stabilization device 102 to the bearing posts 118 and 120 (shown in FIG. 1). One or both of the bushings 218 and 220 may be internally threaded to engage the respective bearing posts 118 and 120. In some embodiments, an external surface of the bushings 218 and 220 may be relatively smooth to facilitate rotation of the respective members 104 and 106 around the bushings.

As illustrated in FIG. 2, the apertures 210 and 214 may be aligned with the first axis 126. The apertures 212 and 216 may be aligned with the second axis 128 and third axis 130, respectively. It is understood that, as the apertures 210, 212, 214, and 216 may be aligned with their respective axes, the pin 108 and bearing posts 118 and 120 may be aligned with the axes due to their insertion into the respective apertures. Alternatively, the pin 108 and bearing posts 118 and 120 may be aligned with their respective axes, and their alignment may result in the alignment of their respective apertures.

Figure 3:
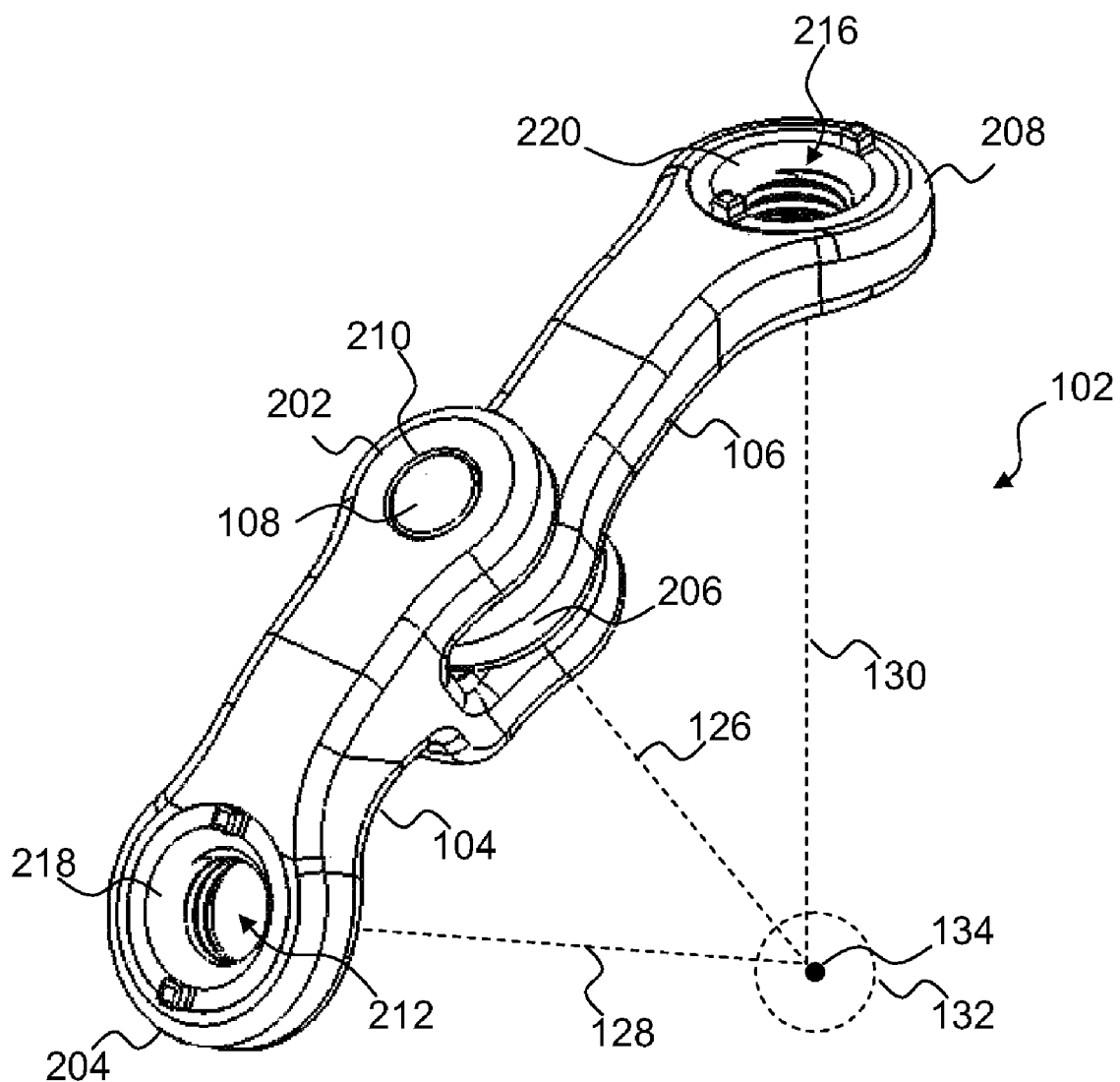
FIG. 3 is a view of the brace illustrated in FIG. 2 in an extended position.

Referring to FIG. 3, the spinal stabilization device 102 of FIG. 2 is illustrated in a fully extended or lengthened position (e.g., during flexion). In the present embodiment, apertures 210, 212, and 216 are aligned with axes 126, 128, and 130, respectively, when in the fully extended position. Accordingly, the axes 126, 128, and 130 may intersect the point 134 and/or move along a surface provided by the area of rotation 132 as previously described.

Figure 4:
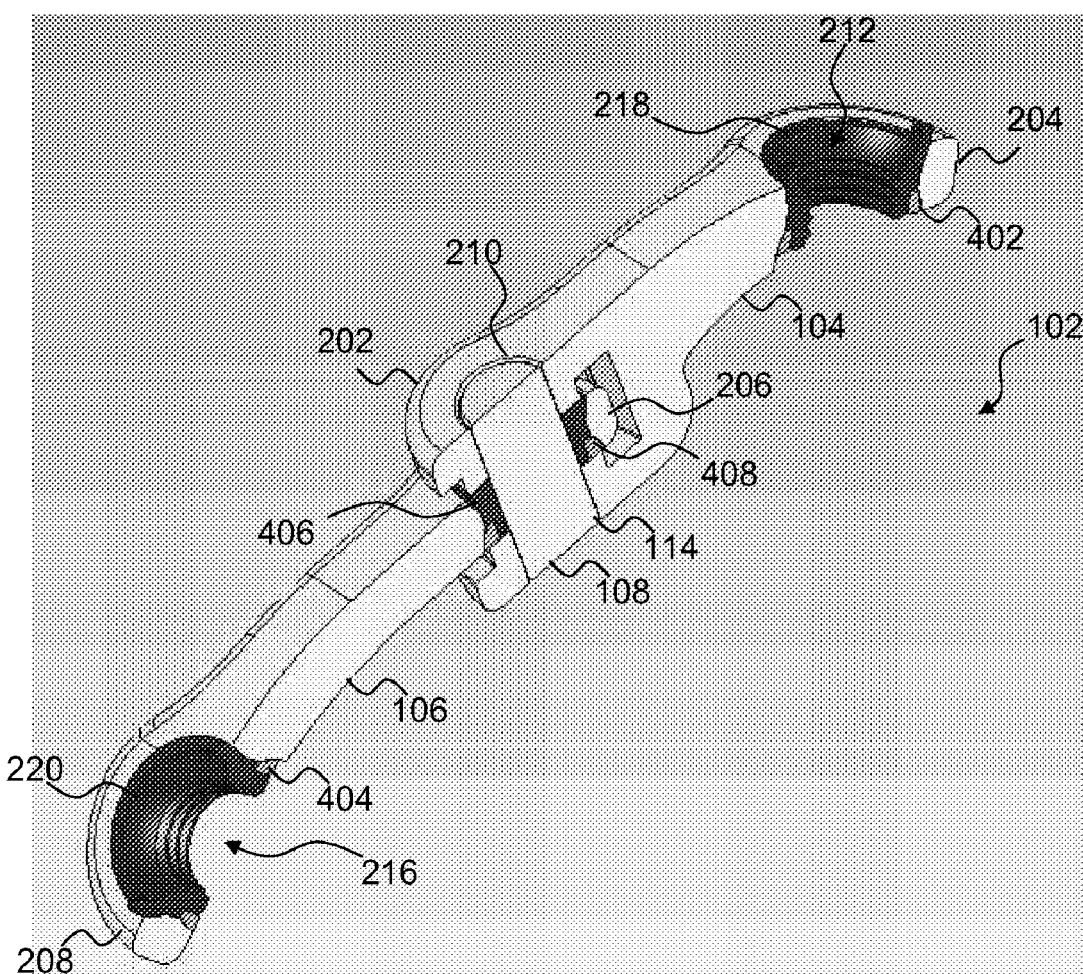
FIG. 4 is a cross-sectional view of the brace of FIG. 3.

With additional reference to FIG. 4, a cross-sectional view of one embodiment of the spinal stabilization device 102 of FIG. 3 is illustrated. As described previously, the members 104 and 106 may be coupled by the pin 108. As illustrated, the bushings 218 and 220 are positioned within the apertures 212 and 216, respectively. In the present example, a bushing cap 402 may abut the bushing 218 and a bushing cap 404 may abut the bushing 220. Also shown, is a bushing 406 in the aperture 214 and an abutting bushing cap 408. In contrast to the illustrated bushings 218 and 220, the bushing 406 may have a smooth bore (e.g., rather than threaded) to facilitate rotation with the pin 208.

The pin 108 may couple the members 104 and 106 via insertion into the apertures 210 and 214, respectively. The bearing posts 118 and 120 may couple the members 104 and 106 to pedicles or other bone (not shown in FIG. 4) via apertures 212 and 216, respectively.

Figure 5:
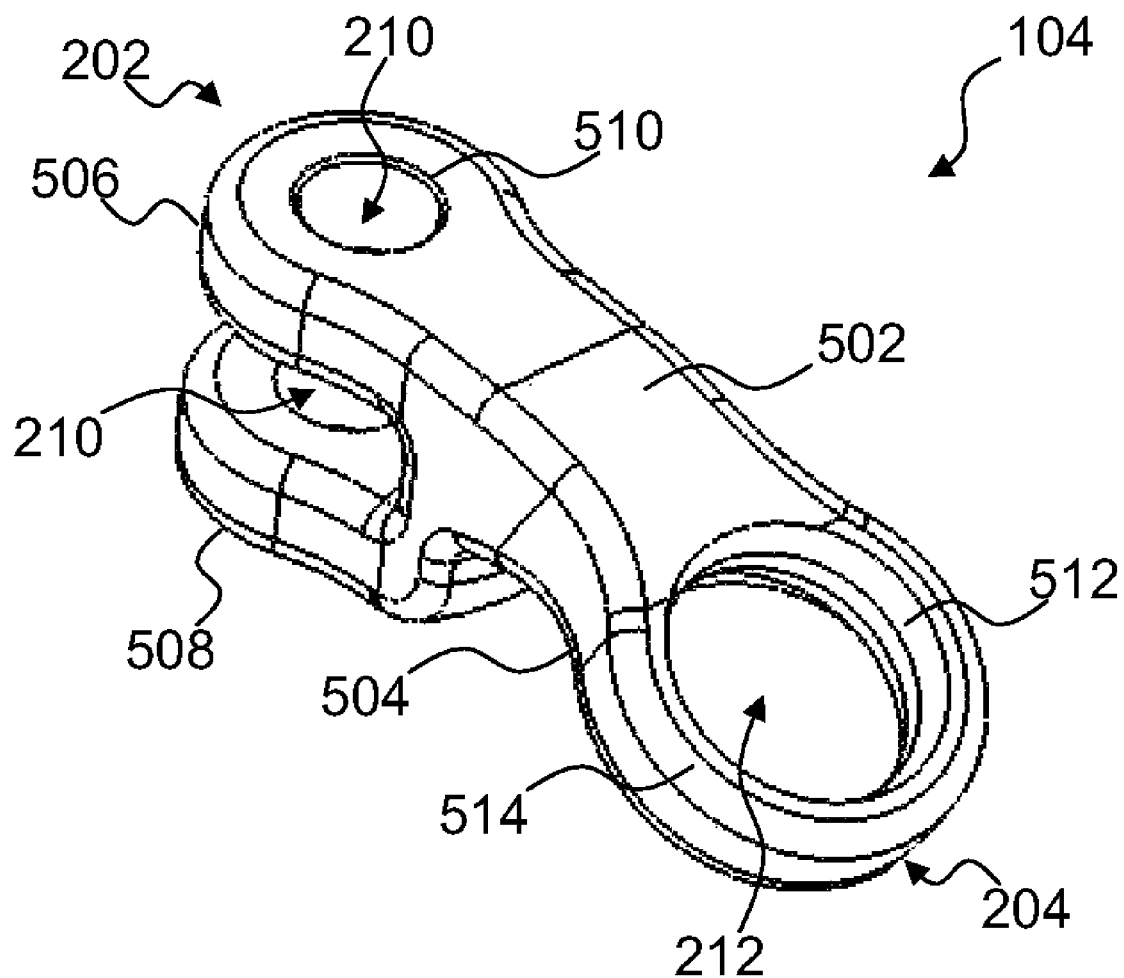
FIG. 5 is a detailed view of one embodiment of a member of the brace of FIG. 2.

Referring to FIG. 5, one embodiment of the member 104 of FIG. 1 is illustrated in greater detail. As described previously, the member 104 may include one or more apertures 210 at the joint end 202 and an aperture 212 at the fastening end 204. In the present example, the member 104 provides a "Y" shape or yoke formed by branches 506 and 508. The branches 506 and 508 may be spaced apart to provide clearance for the end 206 of the member 106. As illustrated, a medial portion of the member 104 (e.g., the portion forming the bottom of the yoke) may be thicker than the fastening end 204 and the branches 506 and 508 forming the joint end 202.

In the present example, an upper surface 502 and a lower surface 504 of the member 104 may be curved to align the apertures 210 and 212 with axes 126 and 128 (shown in FIG. 2), respectively, in order to accommodate the natural movement of the spine. It is understood that the curve may be defined differently depending on such factors as the length of the member 104, the location of the apertures 210 and/or 212, and the desired center of rotation for the dynamic stabilization device 102.

The inner walls 510 of the aperture 210 may be relatively smooth to facilitate rotation of the member 104 with respect to the pin 108. In some embodiments, a bushing (shown in FIG. 4) may be provided to enhance the rotation of the pin 108 (not shown in FIG. 5) within the aperture 210. The inner walls 512 of the aperture 212 may contain ridges, grooves, threads, or other means for engaging the bushing 218 (shown in FIG. 2). The member 104 may also include one or more beveled or otherwise shaped surfaces 514.

Figure 6:
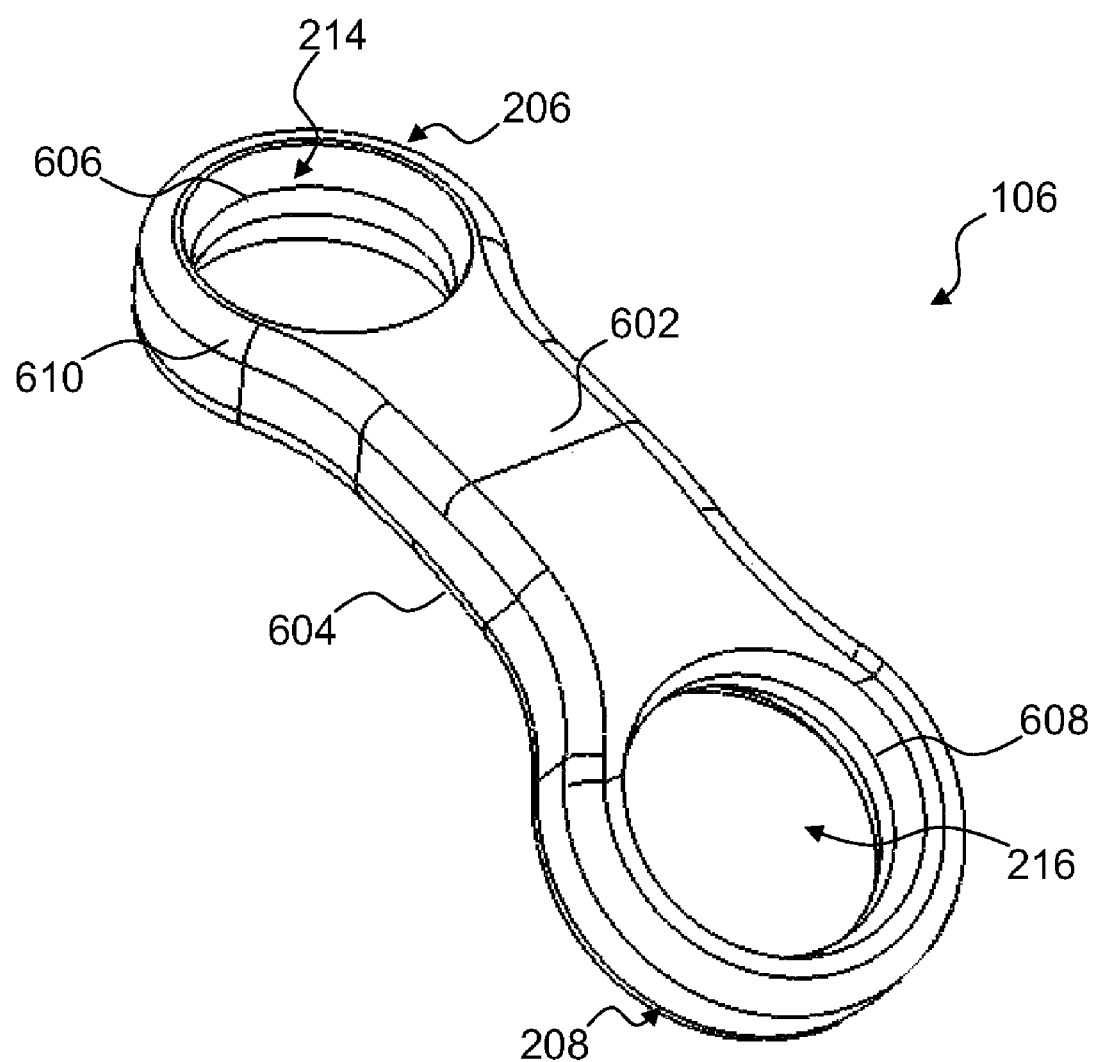
FIG. 6 is a detailed view of one embodiment of a member of the brace of FIG. 2.

Referring to FIG. 6, one embodiment of the member 106 of FIG. 1 is illustrated in greater detail. As described previously, the member 106 may include an aperture 214 at the joint end 206 and an aperture 216 at the fastening end 208. In the present example, the joint end 206 may be sized to fit within a yoke (shown in FIG. 5) of the member 104.

In the present example, an upper surface 602 and a lower surface 604 of the member 102 may be curved to align the apertures 214 and 216 with axes 126 and 130 (shown in FIG. 2), respectively, in order to accommodate the natural movement of the spine. It is understood that the curve may be defined differently depending on such factors as the length of the member 106, the location of the apertures 214 and/or 216, and the desired center of rotation for the dynamic stabilization device 102.

The inner walls 606 of the aperture 214 may be relatively smooth to facilitate rotation of the member 106 with respect to the pin 108. In some embodiments, a bushing (shown in FIG. 4) may be provided to enhance the rotation of the pin 108 within the aperture 214. The inner walls 608 of the aperture 216 may contain ridges, grooves, threads, or other means for engaging the bushing 220 (shown in FIG. 2). The member 106 may also include one or more beveled or otherwise shaped surfaces 610.

Figure 7:
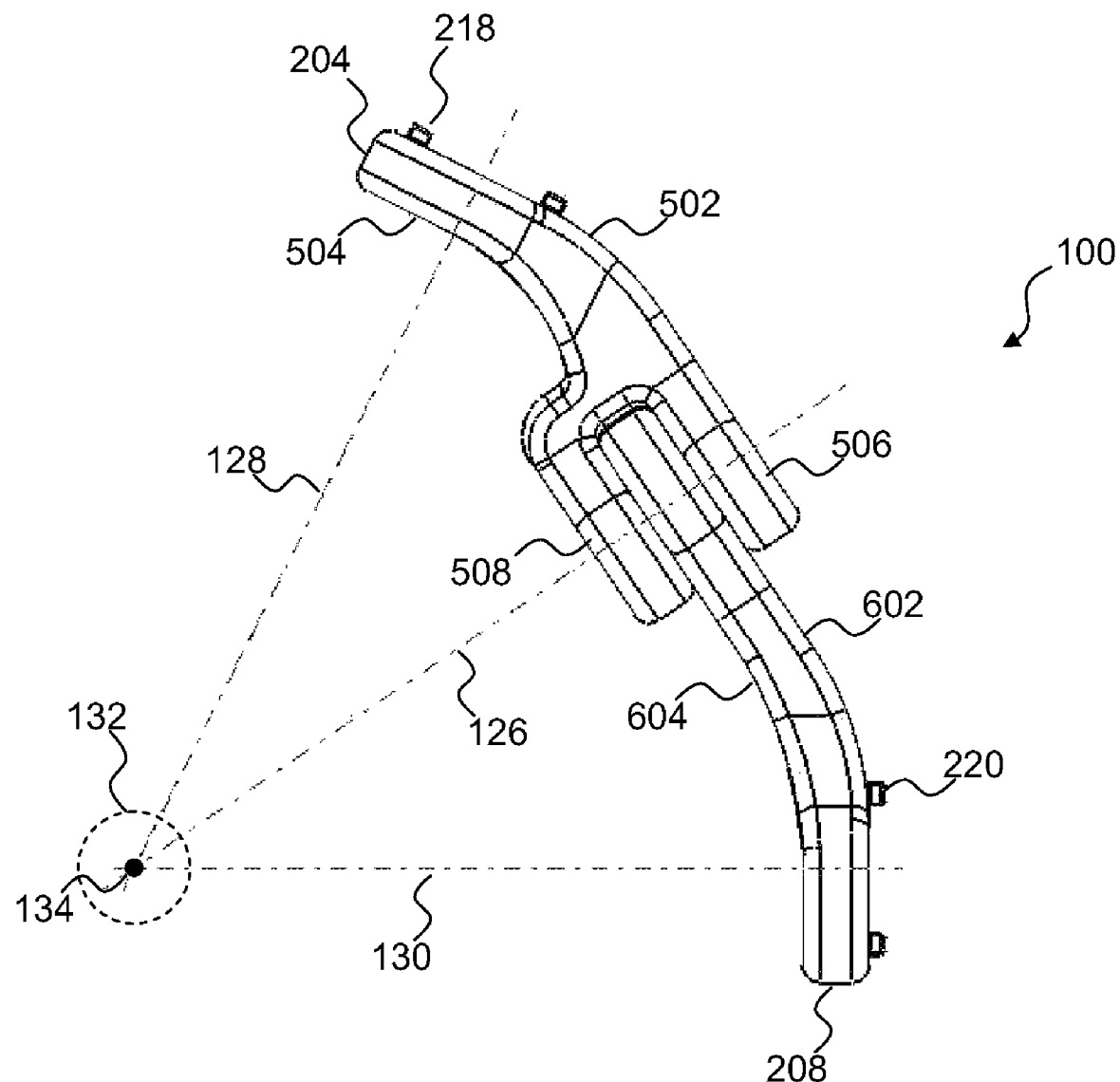
FIG. 7 is a side view of one embodiment of the brace of FIG. 2.

Referring to FIG. 7, a side view of one embodiment of the dynamic stabilization device 102 of FIG. 2 is illustrated. As described previously, the members 104 and 106 may be designed and arranged to align with axes 126, 128, and 130.

Figure 8:
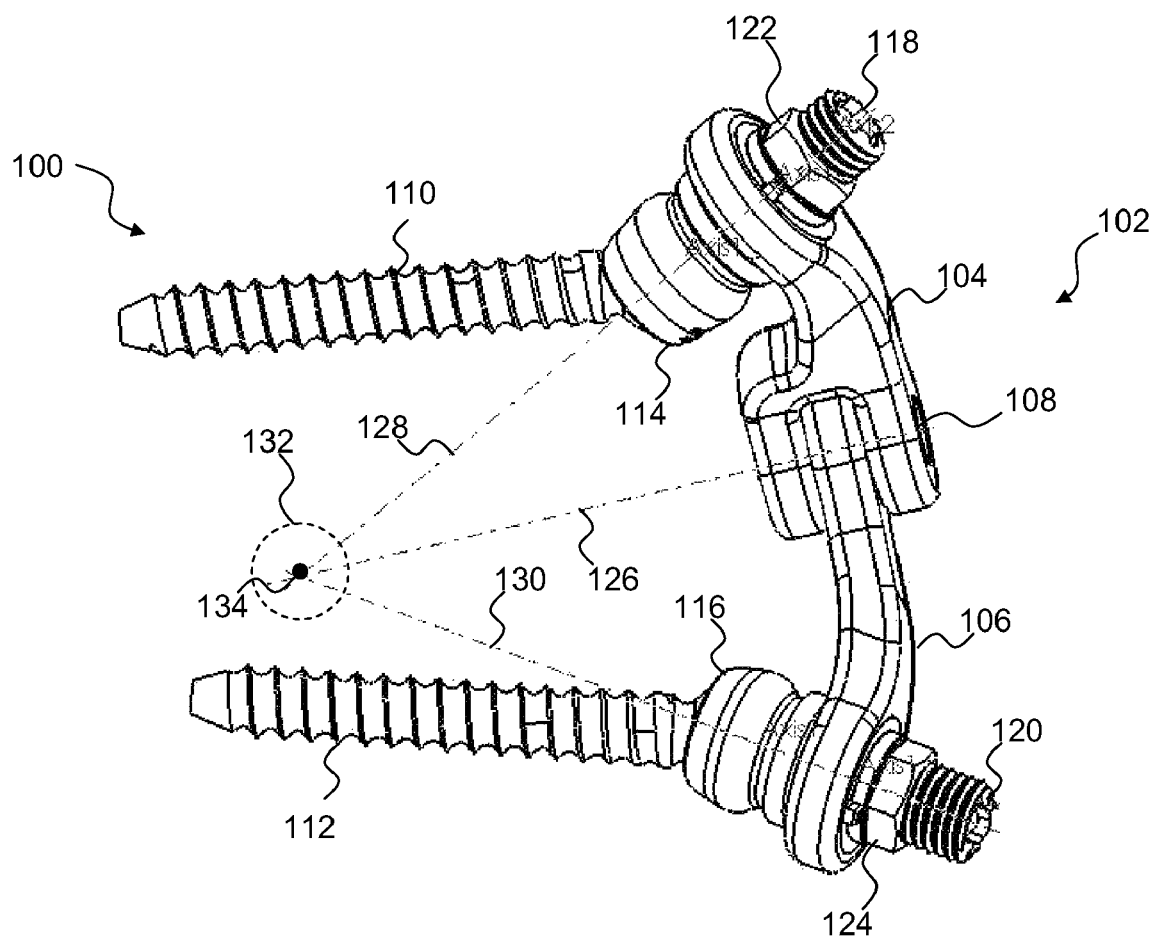
FIG. 8 is a side view of one embodiment of the dynamic stabilization system of FIG. 1.

Referring to FIG. 8, a side view of the dynamic stabilization system 100 of FIG. 1 is illustrated. As described previously, the pin 108 may be aligned with the axis 126, and the bearing posts 118 and 120 may be aligned with axes 128 and 130, respectively. In the present example, the use of polyaxial heads 114 and 116 enables the spinal stabilization device 102 to be oriented to the area 132 even though bone anchors 110 and 112 may be oriented along other axes. This flexibility enables a surgeon to insert the bone anchors 110 and 112 as desired while maintaining the movement of the spinal stabilization device 102 with respect to the area 132 and/or point 134.

Figure 9:
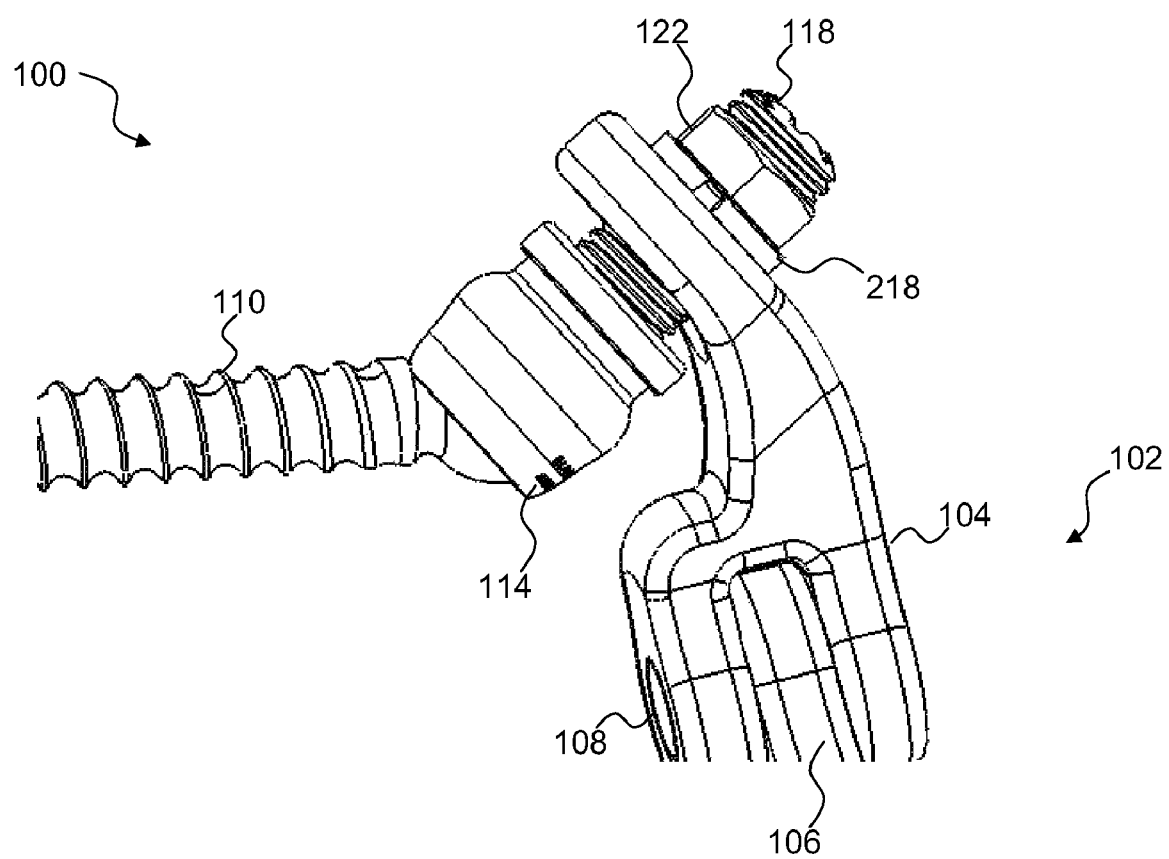
FIG. 9 is an enlarged view of a portion of the dynamic stabilization system of FIG. 8.
Figure 10:
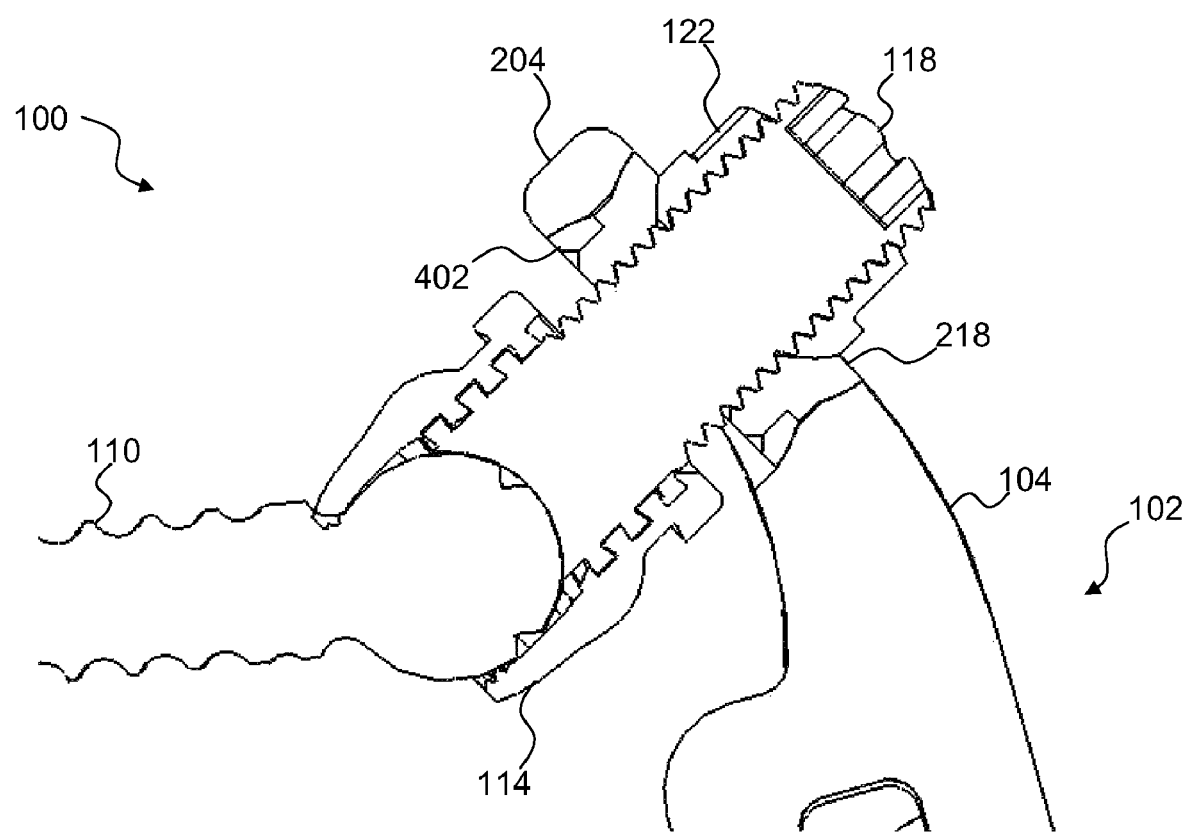
FIG. 10 is a cross-sectional view of the portion of the dynamic stabilization system of FIG. 9.

With additional reference to FIGS. 9 and 10, an enlarged view of a portion of the spinal stabilization device 102 of FIG. 8 is illustrated in side perspective and cross-sectional views, respectively. As shown, the bearing post 118 may extend through the aperture 212 and into the polyaxial head 114. The bushing 218 and bushing cap 402 may be retained in the aperture 212. The locking cap 122 may be used to secure the member 104 to the bearing post 118 at a particular position, enabling a vertical height of the member 104 relative to the polyaxial head 114 to be adjusted. In the present example, a distal portion of the bearing post 118 may be tightened against the bone anchor 110 within the polyaxial head to lock the bone anchor into a desired position with respect to the polyaxial head 114. Prior to the tightening of the bearing post 118, the bone anchor 110 may move relatively freely within the polyaxial head 114. Accordingly, the dynamic stabilization device 102 may be positioned and then the bearing post 118 may be tightened to lock the position of the dynamic stabilization device relative to the polyaxial head 114 and bone anchor 110.

Figure 11A:
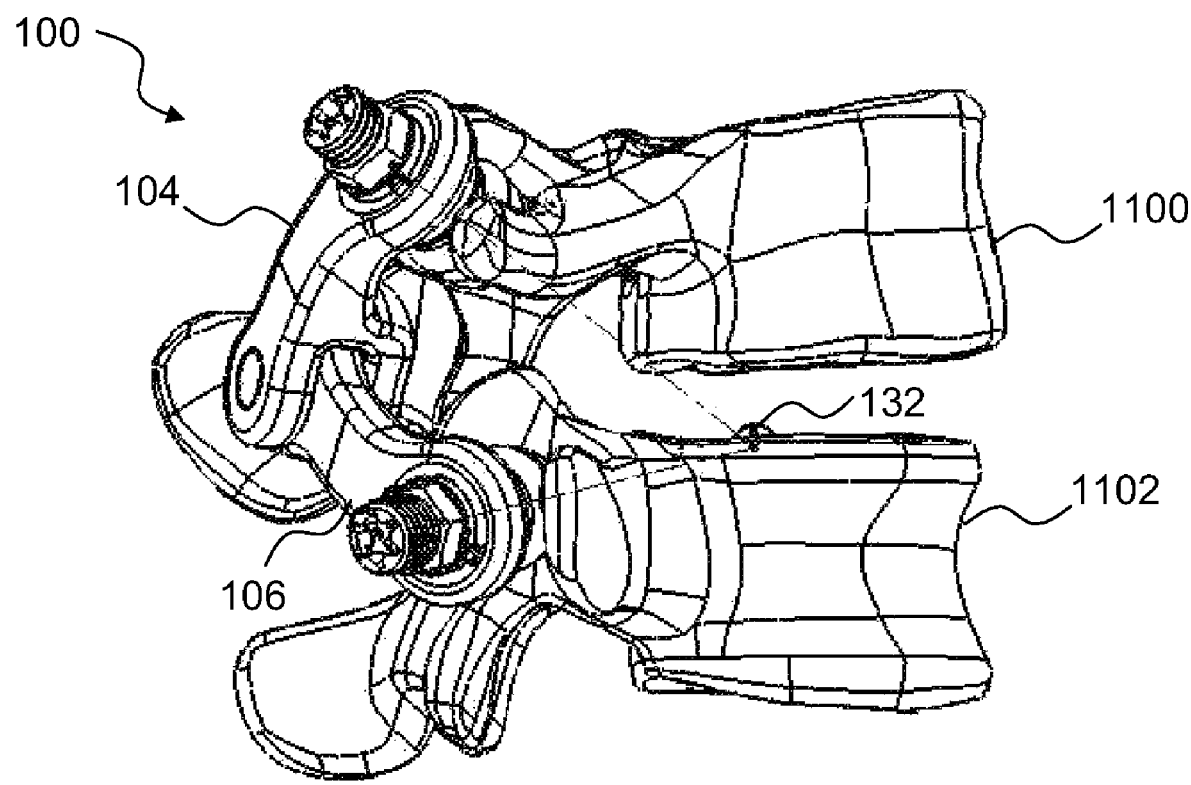
FIG. 11A is a sagittal perspective view of the dynamic stabilization system illustrated in FIG. 1 in a neutral position.
Figure 11B:
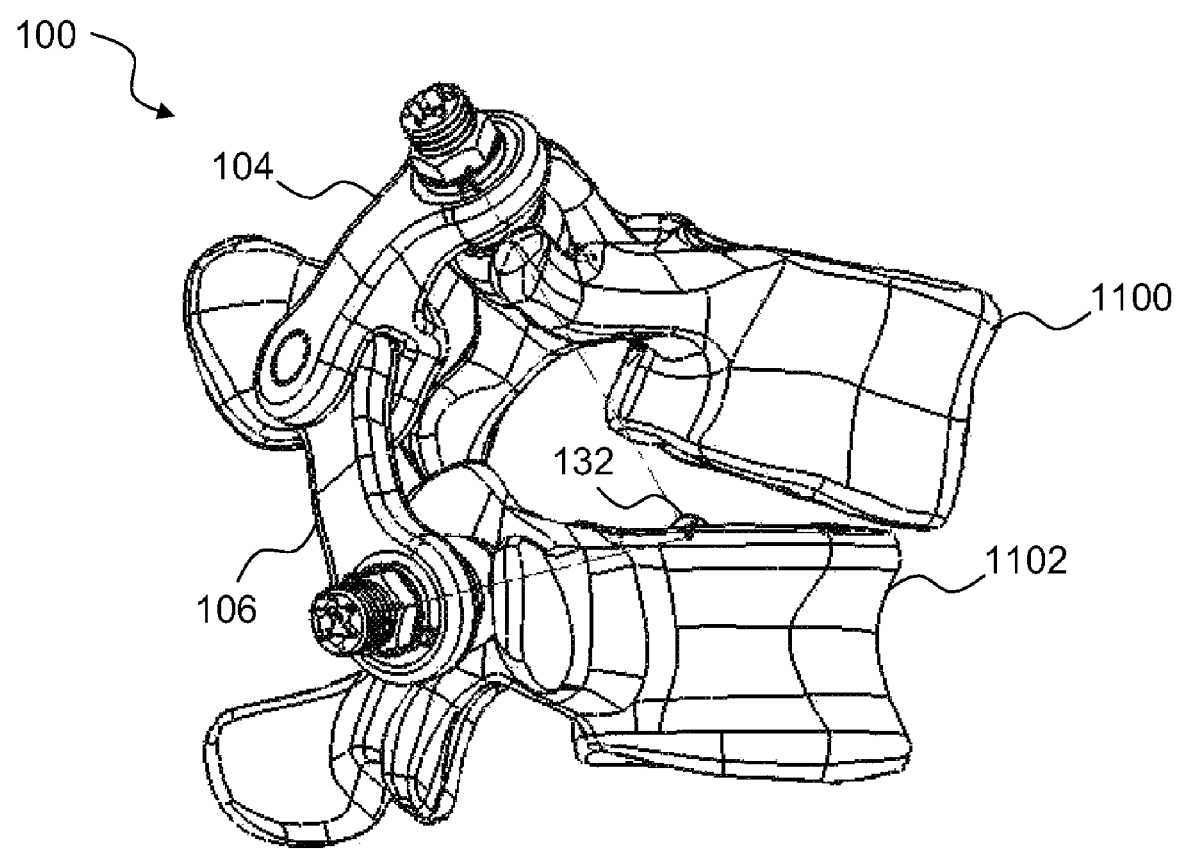
FIG. 11B is a sagittal perspective view of the dynamic stabilization system illustrated in FIG. 1 in a flexion position.

Referring to FIGS. 11A and 11B, there are shown sagittal views illustrating a range of motion and center of rotation between two neighboring vertebrae 1100 and 1102 linked by the spine stabilization system 100 of FIG. 1. FIG. 11A illustrates the spine stabilization system 100 when the two adjacent vertebrae 1100 and 1102 are in a neutral position. FIG. 11B illustrates the spine stabilization system 100 when the two adjacent vertebrae 1100 and 1102 are undergoing flexion (e.g., when the patient is bending forward). As illustrated in FIGS. 11A and 11B, the spine stabilization system 100 maintains alignment with the area 132 (e.g., with a center of rotation or with an area of rotation) regardless of the position of the two vertebrae 1100 and 1102.

Figure 12A:
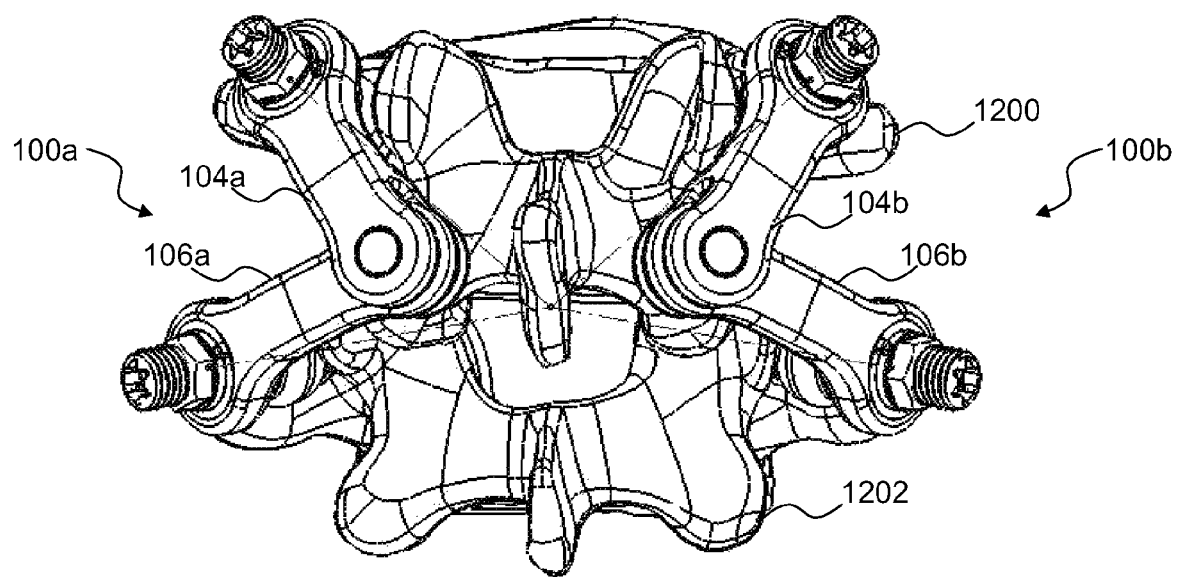
FIG. 12A is a posterior perspective view of the dynamic stabilization system illustrated in FIG. 1 in a neutral position.
Figure 12B:
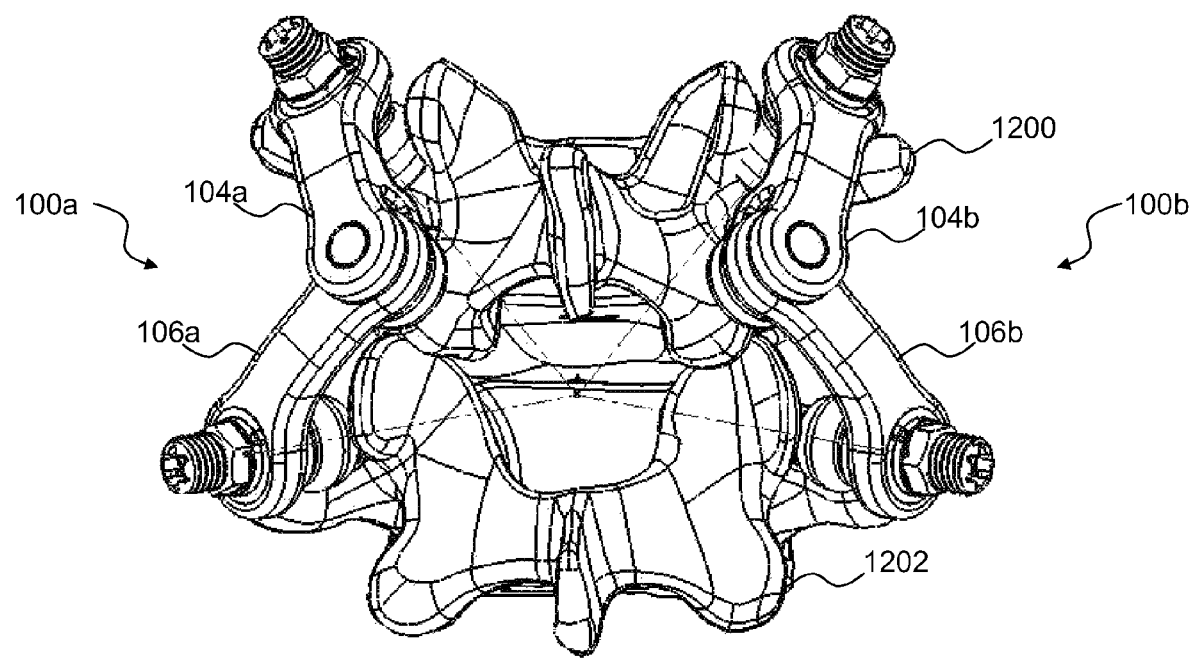
FIG. 12B is a posterior perspective view of the dynamic stabilization system illustrated in FIG. 1 in a flexion position.
Figure 12C:
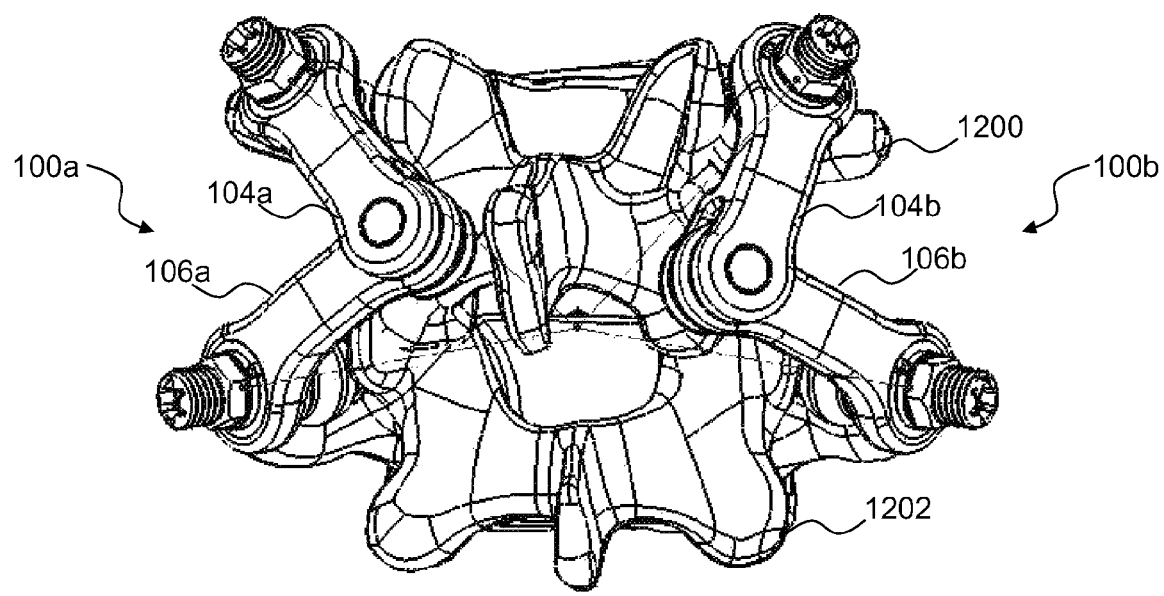
FIG. 12C is a posterior perspective view of the dynamic stabilization system illustrated in FIG. 1 in a rotation position.
Figure 12D:
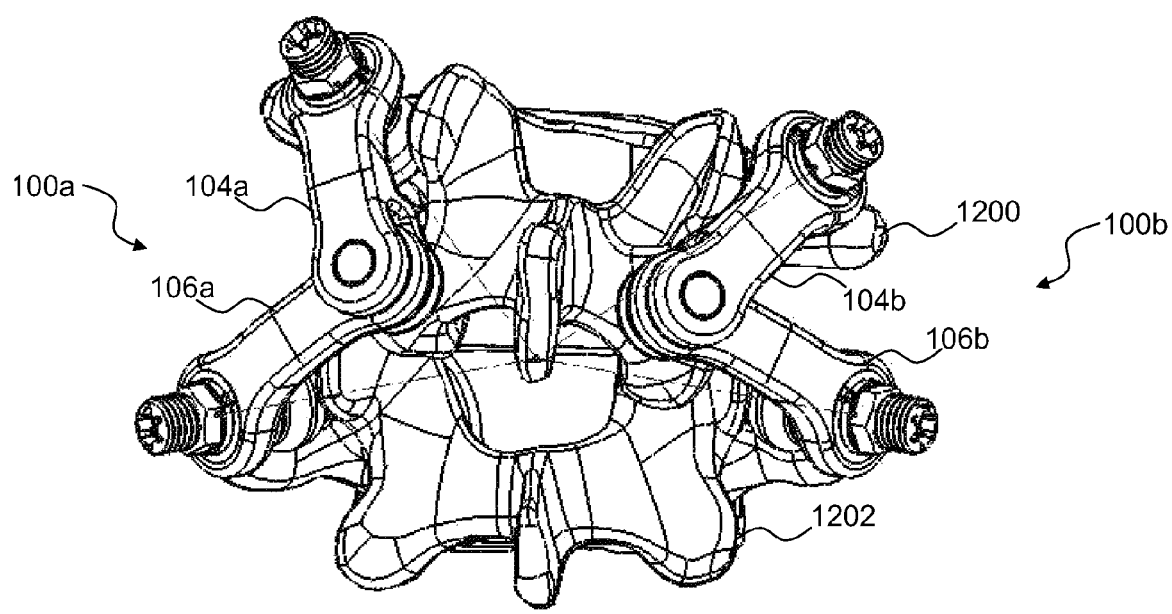
FIG. 12D is a posterior perspective view of the dynamic stabilization system illustrated in FIG. 1 in a lateral bending position.
Figure 12E:
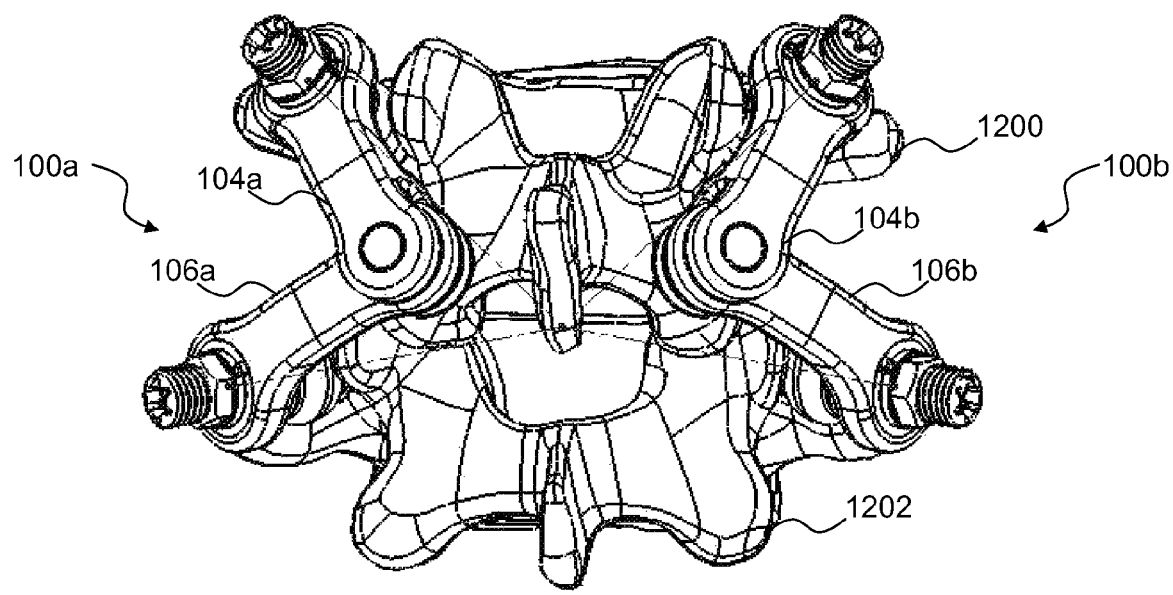
FIG. 12E is a posterior perspective view of the dynamic stabilization system illustrated in FIG. 1 in an extension position.

Referring to FIGS. 12A-12E, there are shown posterior views illustrating a range of motion and center of rotation between two neighboring vertebrae 1200 and 1202 linked by spine stabilization systems 100a and 100b. FIG. 12A illustrates the spine stabilization systems 100a and 100b when the two adjacent vertebrae 1200 and 1202 are in a neutral position. FIG. 12B illustrates the spine stabilization systems 100a and 100b when the two adjacent vertebrae 1200 and 1202 are undergoing flexion (e.g., when the patient is bending forward). FIG. 12C illustrates the spine stabilization systems 100a and 100b when the two adjacent vertebrae 1200 and 1202 are undergoing rotation (e.g., when the patient is turning to the right or left). FIG. 12D illustrates the spine stabilization systems 100a and 100b when the two adjacent vertebrae 1200 and 1202 are in a lateral bending position (e.g., when the patient is bending towards the right or left). FIG. 12E illustrates the spine stabilization systems 100a and 100b when the two adjacent vertebrae 1200 and 1202 are undergoing extension (e.g., when the patient is bending backward). As illustrated in FIGS. 12A-12E, the spine stabilization systems 100a and 100b maintain alignment with the area 132 (e.g., with a center of rotation or with an area of rotation) regardless of the position of the two vertebrae 1200 and 1202.

Figure 13:
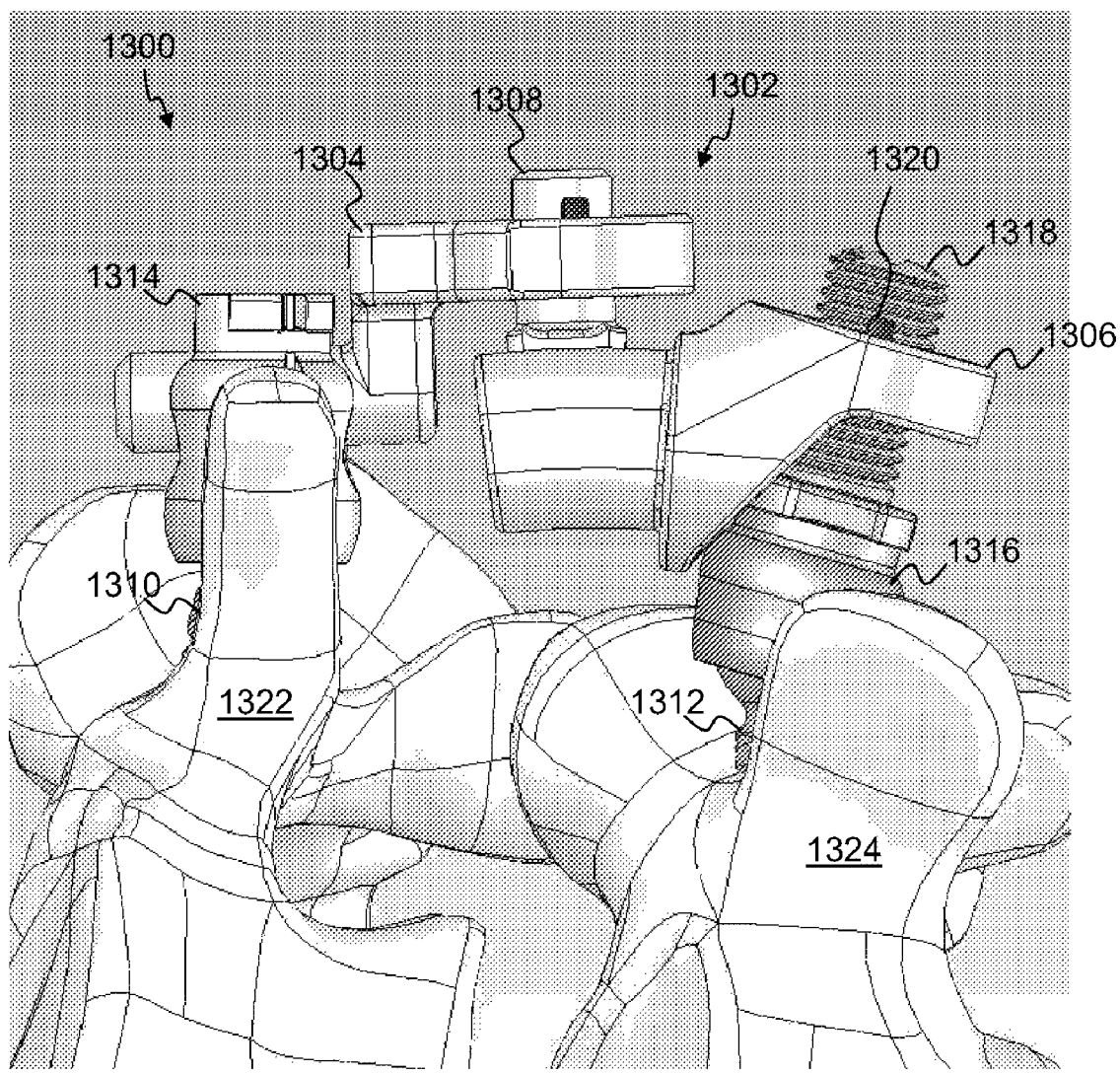
FIG. 13 is a perspective view of another embodiment of a dynamic stabilization system.

Referring to FIG. 13, in another embodiment, a spine stabilization system 1300 is illustrated. The spine stabilization system 1300 may be fitted to varying anatomies while providing a consistent range of motion, consistent dampening forces at the extremes of motion, alignment with a desired center of rotation (e.g., 60-70% A-P), and co-alignment of left and right systems. For example, the spine stabilization system 1300 may provide height adjustment, spherical functionality, and/or sliding adjustment for variations in a patient's anatomy.

The dynamic stabilization device 1302 may include two anchor members 1304 and 1306 coupled by a sliding member 1308. The sliding member 1308 may enable the two anchor members 1304 and 1306 to move with respect to one another, as will be described later in greater detail.

Each anchor member 1304 and 1306 may be secured to a portion of a vertebral body 1322 and 1324, respectively, such as a pedicle, via a fastening element such as a bone anchor (e.g., a pedicle screw) 1310 and 1312, respectively. In the present example, each bone anchor 1310 and 1312 may include or be coupled to a polyaxial head 1314 and 1316, respectively. The anchor members 1304 and 1306 may then be coupled to their respective polyaxial head 1314 and 1316 to link each anchor member with a bone anchor. For example, the polyaxial head 1314 may include a slot or other opening for receiving a portion of the anchor member 1304. The polyaxial head 1316 may be configured to receive a bearing post 1318 (e.g., a locking screw), and the anchor member 1306 may couple to the polyaxial head via the bearing post and a threaded bearing element 1320. It is understood that while the present example illustrates different configurations for coupling the anchor members 1304 and 1306 to their respective polyaxial heads 1314 and 1316, a single configuration may be used in some embodiments.

Although not shown, the polyaxial heads 1314 and 1316 and/or the anchor members 1304 and 1306 may be aligned with a center of rotation as described with respect to the dynamic stabilization device 100 of FIG. 1. Accordingly, two and three dimensional movement of the anchor members 1304 and 1306 may be constrained to ensure that axes of the polyaxial heads 1314 and 1316 and/or the anchor members 1304 and 1306 remain aligned with the center of rotation.

Figure 14:
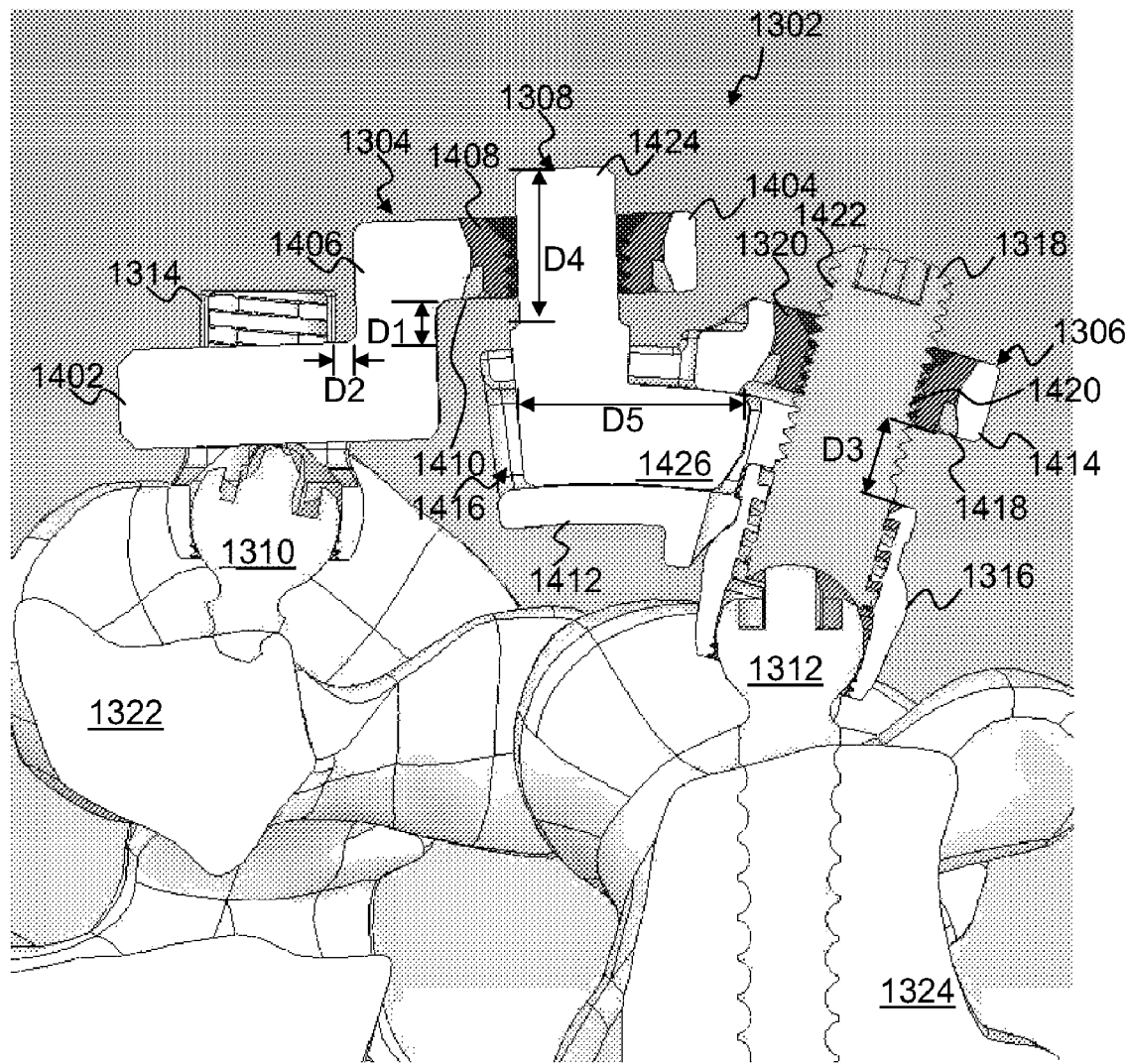
FIG. 14 is a cross-sectional view of one embodiment of the dynamic stabilization system of FIG. 13.

Referring to FIG. 14, a cross-sectional view of one embodiment of the dynamic stabilization device 1302 of FIG. 13 is illustrated. As stated with respect to FIG. 13, the dynamic stabilization device 1302 may include two anchor members 1304 and 1306 that are coupled via the sliding member 1308.

In the present example, the anchor member 1304 may include an adjustable anchor portion 1402 and a dynamic portion 1404 joined by a middle portion 1406. While the middle portion 1406 is illustrated as connecting to the adjustable anchor portion 1402 and dynamic portion 1404 at substantially ninety degree angles in the present embodiment, it is understood that other angles may be used. Furthermore, it is understood that a distance D1 representing a distance (relative to the positioning illustrated in FIG. 14) between the adjustable anchor portion 1402 and dynamic portion 1404 may be varied from that shown.

The adjustable anchor portion 1402 of the anchor member 1304 may be sized to enter a slot (1804 of FIG. 18) in the polyaxial head 1314. As will be described later, the adjustable anchor portion 1402 may be moved within the polyaxial head 1314 until a desired position is attained and then locked into place. Accordingly, a distance D2 representing a distance between the polyaxial head 1314 and the middle portion 1406 may be varied as a position of the adjustable anchor portion 1402 varies with respect to the polyaxial head.

The dynamic portion 1404 of the anchor member 1304 may include an opening containing a threaded or non-threaded bearing element 1408 coupled (e.g., welded) to a bearing element 1410. The bearing element 1410 may serve to retain the bearing element 1408 in the opening. The bearing element 1408 may include a bore sized to receive a portion of the sliding element 1308. In the present example, the bearing element 1408 may be sized to allow the sliding element 1308 to rotate and slide within the bearing element's bore, enabling the anchor member 1304 to move relative to the sliding member 1308.

The anchor member 1306 may include a cavity portion 1412 and an adjustable anchor portion 1414. The cavity portion 1412 may include a cavity 1416 running substantially along a longitudinal axis of the cavity portion 1412, and the cavity 1416 may be sized to receive a portion of the sliding member 1308. As will be described below, an upper part of the cavity portion 1412 (e.g., facing the underside of the dynamic portion 1404 of the anchor member 1304) may include an opening (1606 of FIG. 16) to allow the sliding member 1308 to move within the cavity 1416.

The adjustable anchor portion 1414 may include an opening containing the threaded bearing element 1320 coupled (e.g., welded) to a bearing element 1418. The bearing element 1418 may serve to retain the threaded bearing element 1320 in the opening. The threaded bearing element 1320 may include internal threads 1420 configured to engage external threads 1422 of the bearing post 1318. A locking cap (1502 of FIG. 15A) may be used to lock a position of the anchor member 1306 relative to the bearing post 1318 at a variable distance D3 between the adjustable anchor portion 1414 and the polyaxial head 1316.

Figure 15A:
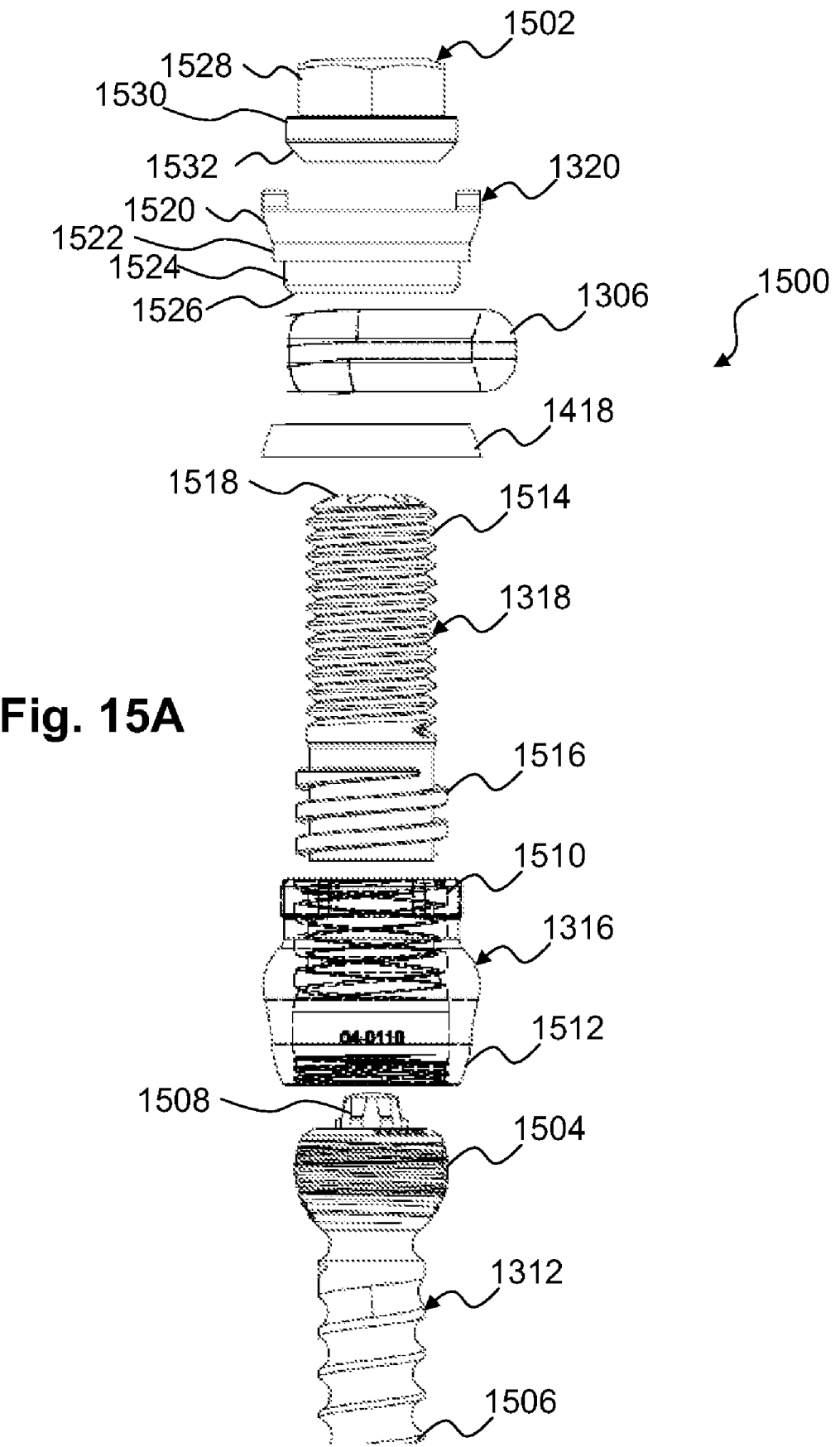
FIG. 15A is an exploded view of one embodiment of a locking assembly that may be used with the dynamic stabilization system of FIG. 13.

With additional reference to FIG. 15A, one embodiment of a locking assembly 1500 that may be used to couple the anchor member 1306 to the bone anchor 1312 is illustrated in greater detail in a cross-sectional view. The locking assembly may include the bone anchor 1310 (e.g., a pedicle screw), polyaxial head 1316, bearing post 1318, threaded bearing element 1320, bearing element 1418, and locking cap 1502.

The bone anchor 1312 may include a proximal portion 1504 and a distal portion 1506. In the present example, the proximal portion 1504 may include a reverse thread that engages a compatible thread form within the polyaxial head 1316. When coupled, the polyaxial head 1316 may move in relation to the bone anchor 1312. The bone anchor 1312 may further include an engagement portion 1508.

The polyaxial head 1316 may include a proximal portion 1510 and a distal portion 1512, both of which may be threaded. The proximal portion 1510 may include a thread form different from that of the distal portion 1512. In the present example, the distal portion 1512 may be threaded to receive the reverse thread of the proximal portion 1504 of the bone anchor 1312. The proximal portion 1510 may be threaded to receive a portion of the bearing post 1318. The threads of the proximal portion 1510 may be designed with anti-splay characteristics. For example, the threads may be grooved to accept a dovetail shaped thread. In some embodiments, the proximal portion 1510 may be reverse threaded.

The bearing post 1318 may include a proximal portion 1514 and a distal portion 1516, both of which may be threaded. The proximal portion 1514 may include a thread form different from that of the distal portion 1516. In the present example, the distal portion 1516 may include a thread form configured to engage the thread form of the proximal portion 1510 of the polyaxial head 1316. Although the thread form is not reverse threaded in the present embodiment, it is understood that it may be reverse threaded in other embodiments. The proximal portion 1514 may be threaded to engage the threaded bearing element 1320 and locking cap 1502. The proximal end of the bearing post 1318 may include one or more features 1518. Such features 1518 may, for example, be used to engage a tool for rotating the bearing post 1318.

The threaded bearing element 1320 may include internal threads (1534 of FIG. 15B) configured to engage the proximal portion 1514 of the bearing post 1318. In the present example, the threaded bearing element 1320 may have an exterior surface of varying diameters, including a proximal portion 1520, a first intermediate portion 1522, a second intermediate portion 1524, and a distal portion 1526. As will be illustrated in FIG. 15B, the distal portion 1526 and second intermediate portion 1524 may abut the bearing element 1322 and the proximal portion 1520 and first intermediate portion 1522 may abut the anchor member 1306. As the exterior surface of the threaded bearing element 1320 may be non-threaded, the anchor member 1306 may rotate around the threaded bearing element.

The locking cap 1502 may include internal threads (1536 of FIG. 15B) configured to engage the proximal portion 1514 of the bearing post 1318. In the present example, the locking cap 1502 may have an exterior surface of varying diameters, including a proximal portion 1528, an intermediate portion 1530, and a distal portion 1532. As will be illustrated in FIG. 15B, the intermediate portion 1530 and distal portion 1532 may abut an interior surface of the threaded bearing element 1320 and the proximal portion 1528 may provide a surface for engaging a tool used to tighten the locking cap 1502.

Figure 15B:
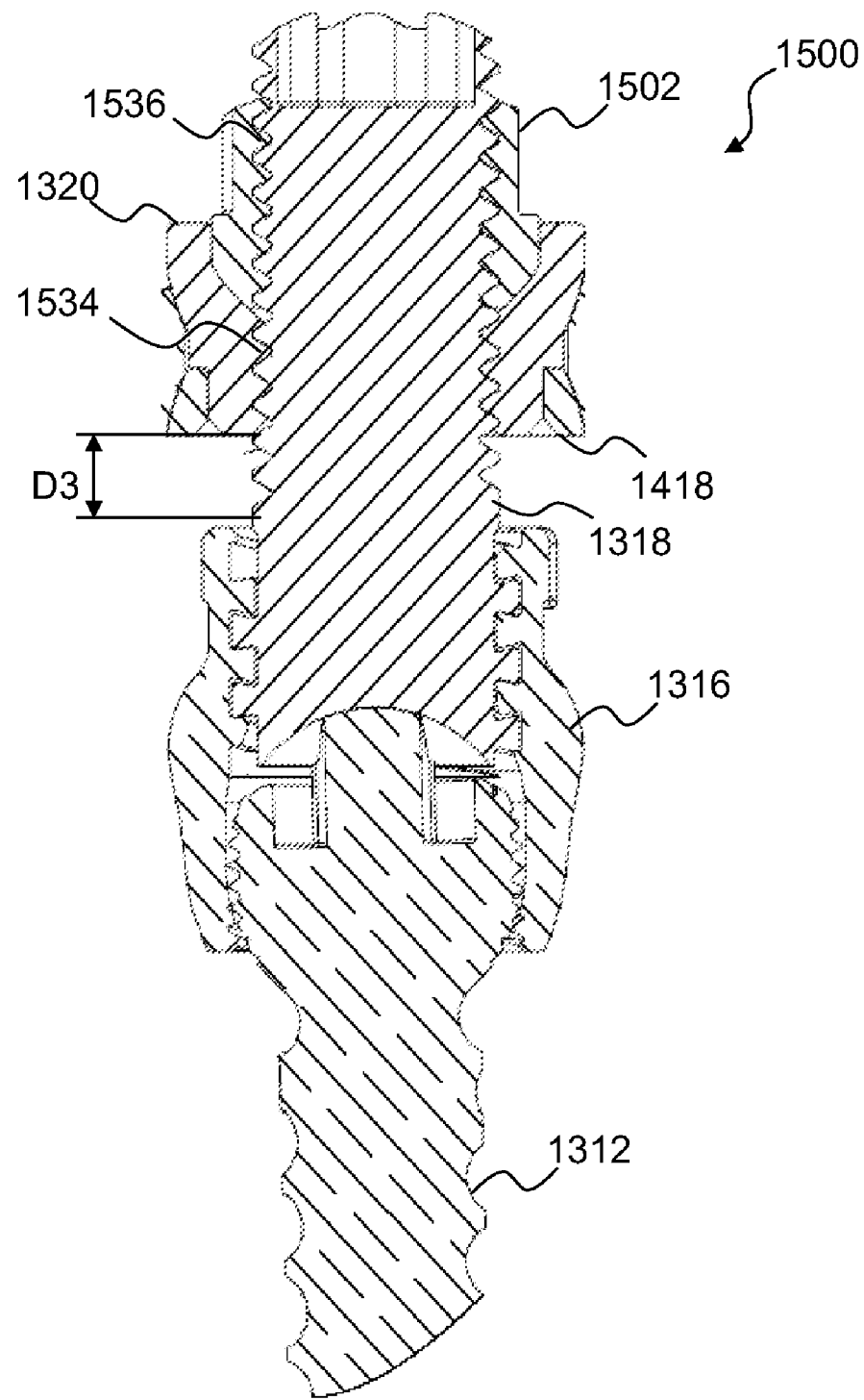
FIG. 15B is a cross-sectional view of one embodiment of the locking assembly of FIG. 15A in an assembled state.

With additional reference to FIG. 15B, one embodiment of the locking assembly 1500 of FIG. 15A is illustrated in an assembled form. As stated previously, the polyaxial head 1316 may generally move relative to the bone anchor 1312. However, once the polyaxial head 1316 is positioned as desired with respect to the bone anchor 1312, it may be desirable to lock the polyaxial head into position. Accordingly, the bearing post 1318 may be inserted into the polyaxial head 1316 so that the threads of the distal portion 1516 of the bearing post engage the threads of the proximal portion 1510 of the polyaxial head. The bearing post 1318 may then be tightened until the distal end (which may be concave in the present example) contacts the engagement portion 1508 of the bone anchor 1312. This locks the position of the polyaxial head 1316 relative to the bone anchor 1312.

As can be seen in FIG. 15B, the threaded bearing element 1320 may not contact the polyaxial head 1316. More specifically, the position of the threaded bearing element 1320 may be adjusted along a longitudinal axis of the bearing post 1318 to vary the distance D3 that exists between the threaded bearing element and the polyaxial head 1316. This enables a height of the anchor member 1306 relative to the polyaxial head 1316 to be varied and allows for adjustments to be made to the dynamic stabilization device 1302.

The locking cap 1502 may be rotated along the longitudinal axis of the bearing post 1318 to the desired position and tightened against the threaded bearing element 1320. As illustrated, intermediate portion 1530 and distal portion 1532 of the exterior surface of the locking cap 1502 may enter a bore of the threaded bearing element 1320 and lock against an internal surface of the threaded bearing element. This may lock the threaded bearing element 1320 into place relative to the polyaxial head 1316 and may maintain the distance D3 as set.

Referring again to FIG. 14, the sliding portion 1308 may include a first portion 1424 that extends into the dynamic portion 1404 of the anchor member 1304 and a second portion 1426 that extends into the cavity portion 1412 of the anchor member 1306. The first portion 1424 may be configured with a length D4 that may fit within the bearing element 1408, while the second portion 1426 may be configured with a length D5 that may fit within the cavity 1416. In the present example, the first and second portions 1424 and 1426 form a substantially ninety degree angle, but it is understood that other angles may be used.

The first and second portions 1424 and 1426 may be captured within the dynamic portion 1404 and cavity portion 1412 by the positioning of the anchor members 1304 and 1306 and/or by other means. For example, a maximum change of position between the vertebral bodies 1322 and 1324 along a longitudinal axis of the portion 1424 may be less than the length D4. Similarly, a maximum change of position between the vertebral bodies 1322 and 1324 along a longitudinal axis of the portion 1426 may be less than the length D5.

In some embodiments, additional means (e.g., a retaining ring, retaining pin, or elastic sleeve) may be provided to capture the first portion 1424 and/or second portion 1426 within the dynamic portion 1404 and cavity portion 1412, respectively.

Figure 16:
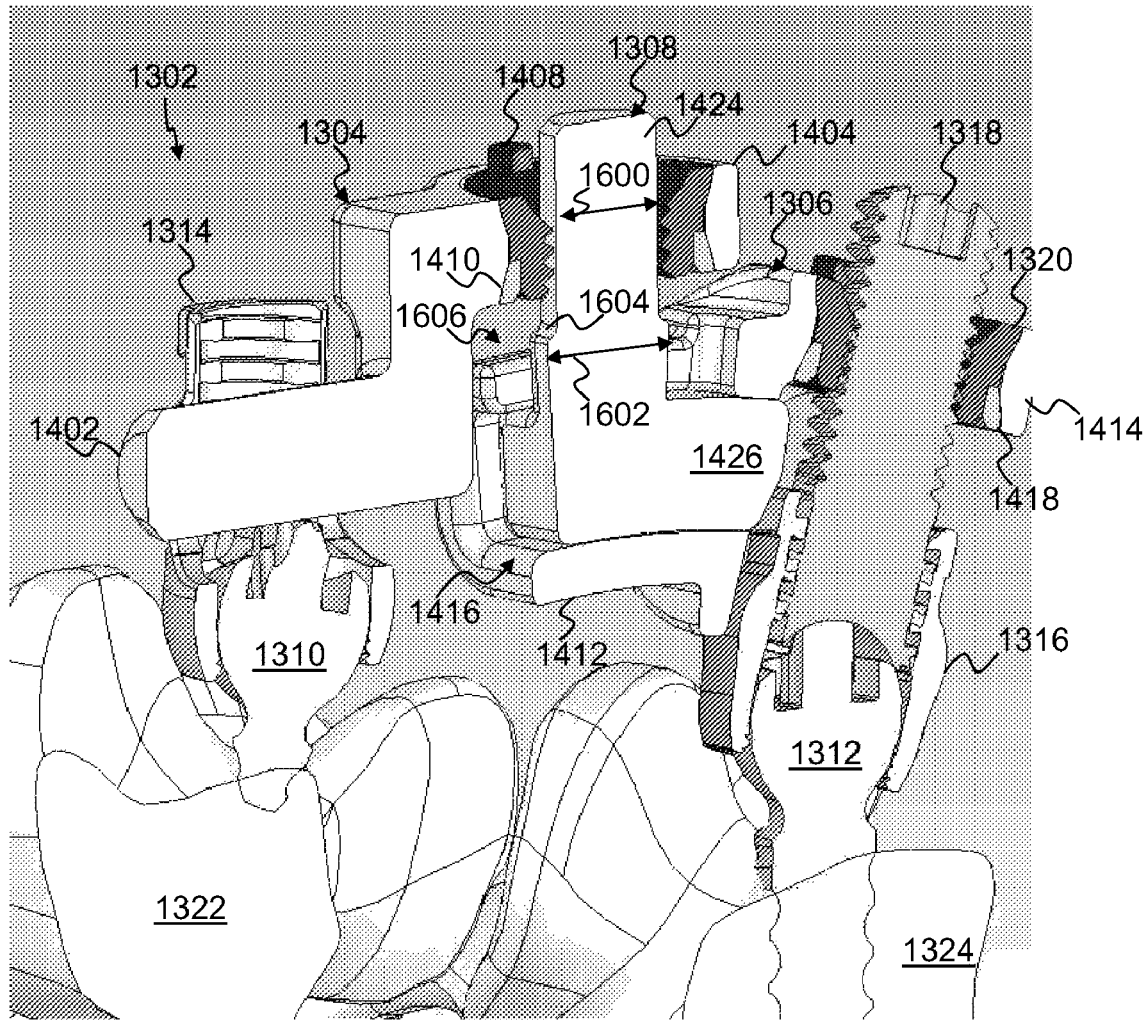
FIGS. 16 and 17 are a cross-sectional views of one embodiment of the dynamic stabilization system of FIG. 13.

With additional reference to FIG. 16, another cross-sectional view of the dynamic stabilization device 1302 illustrates the sliding member 1308 in greater detail. As can be seen, in the present embodiment, the portion 1424 of the sliding member 1308 may have a first diameter represented by arrow 1600 and a second diameter represented by arrow 1602. The first diameter 1600, which is sized to fit within the bearing element 1408, may be smaller than the second diameter 1602, which is larger than the bore of the bearing element. Accordingly, the diameter 1602 may prevent the dynamic portion 1404 from contacting the cavity portion 1412. A sloped neck 1604 may join the two diameters. A slot 1606 may be sized to enable movement of the portion 1424 along a longitudinal axis of the cavity portion 1412.

It is understood that the illustrated cross-sections may be varied. For example, as shown in FIG. 16, the portion 1424 is substantially cylindrical and the portion 1426 is substantially rectangular. Similarly, the adjustable anchor portion 1402 is substantially cylindrical. However, these cross-sectional shapes are for purposes of example only and other shapes may be used. Furthermore, various features (e.g., grooves and/or protrusions) may be provided on the surface of the adjustable anchor portion and/or other components.

Figure 17:
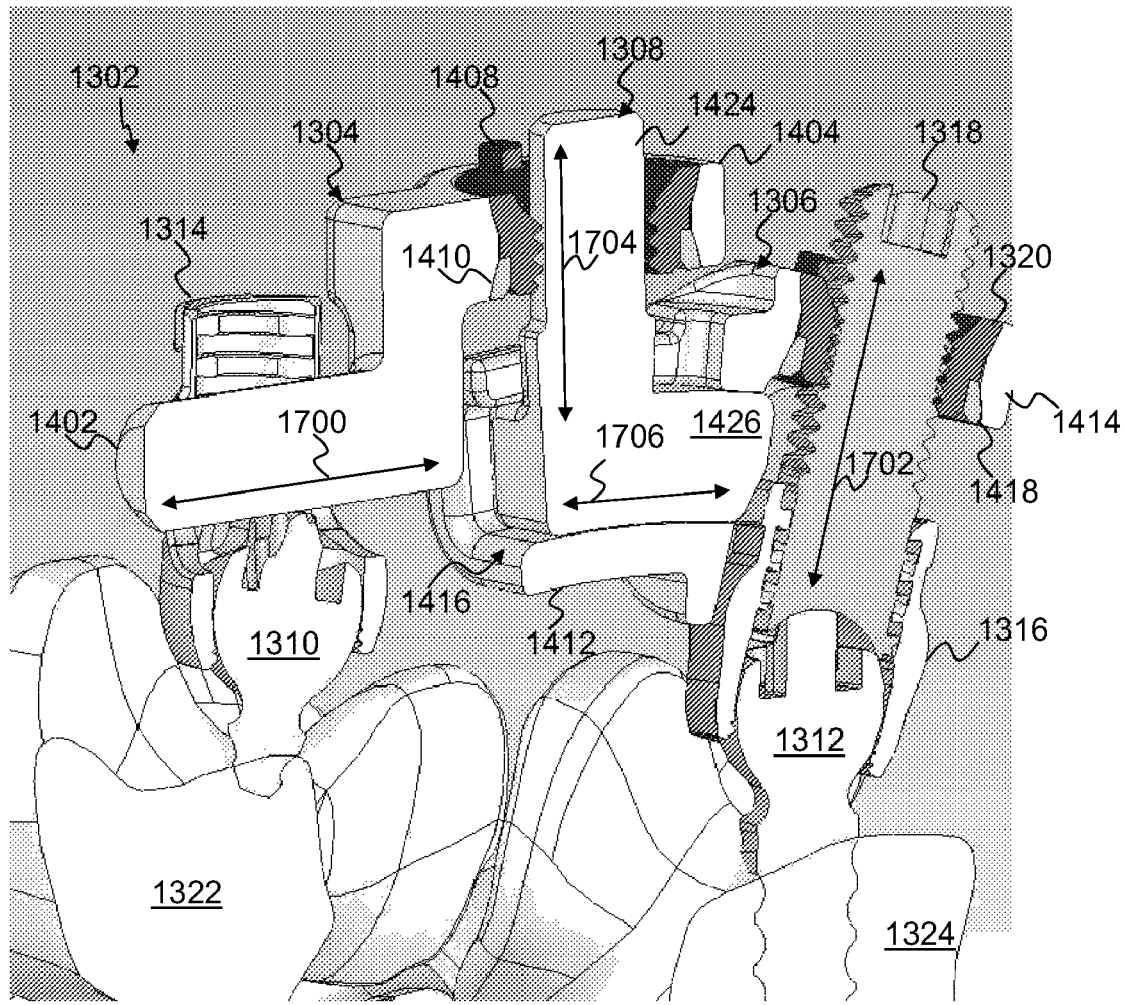

Referring to FIG. 17, while some portions of the dynamic stabilization device 1302 may be locked into place after positioning, other portions may move within a defined range even after positioning. For example, during insertion of the dynamic stabilization device 1302, the adjustable anchor portion 1402 may be inserted into the polyaxial head 1314. Adjustment of the anchor member 1304 may then occur along a longitudinal axis (represented by arrow 1700) of the adjustable anchor portion 1402. Once correctly positioned, a locking nut or other locking means configured to engage threads within the polyaxial head 1314 may be tightened. The tightening may lock the adjustable anchor portion 1402 into place within the polyaxial head 1314. Accordingly, varying distances between the vertebral bodies 1322 and 1324 may be accounted for during the implantation procedure using the adjustable anchor portion 1402. As illustrated, the tightening may also force the adjustable anchor portion 1402 against the bone anchor 1310, preventing movement between the bone anchor and the polyaxial head 1314. In other embodiments, the bone anchor 1310 and polyaxial head 1314 may be locked into place prior to locking the adjustable anchor portion 1402 into place.

Similarly, during insertion of the dynamic stabilization device 1302, the adjustable anchor portion 1414 may be positioned as desired along a longitudinal axis (represented by arrow 1702) of the bearing post 1318. Once correctly positioned, the adjustable anchor portion 1414 may be locked into placed with respect to the polyaxial head 1316 using the locking cap 1502 (shown in FIG. 15B), preventing further movement along the longitudinal axis 1702. Accordingly, the anchor portion 1304 may be locked into position relative to the bone anchor 1310 and the anchor portion 1306 may be locked into position relative to the bone anchor 1312. As described previously, the adjustable anchor portion 1414 of the anchor member 1306 may still be able to rotate around the longitudinal axis 1702.

Even after movement along the longitudinal axes 1700 and 1702 is stopped, movement may occur between the components of the dynamic stabilization device 1302. For example, although the anchor portions 1304 and 1306 may be locked into position relative to their respective bone anchors 1310 and 1312, they may still move with respect to one another due to the sliding member 1308. For example, the anchor members 1304 and 1306 may move with respect to one another in a first direction along a longitudinal axis (represented by arrow 1704) of the portion 1424 as the portion 1424 moves within the bearing element 1408. The anchor member 1304 may also rotate at least partially around the longitudinal axis 1704.

Similarly, the anchor members 1304 and 1306 may move with respect to one another in a second direction along a longitudinal axis (represented by arrow 1706) of the portion 1426 as the portion 1426 moves within the cavity 1416. It is understood that the longitudinal axis 1706 (and the other longitudinal axes) may actually be curved, and so the movement may be along a curved path rather than a straight line. Accordingly, the anchor member 1304 may rotate and slide with respect to the anchor member 1306 within the range provided by the sliding member 1308, and the anchor member 1306 may rotate with respect to the bearing post 1318. As discussed above, such movement may be limited. It is understood that such movement may occur simultaneously or separately (e.g., rotation around and/or movement may occur around one or both axes 1702 and 1704, and/or along one or both axes 1704 and 1706).

Figure 18:
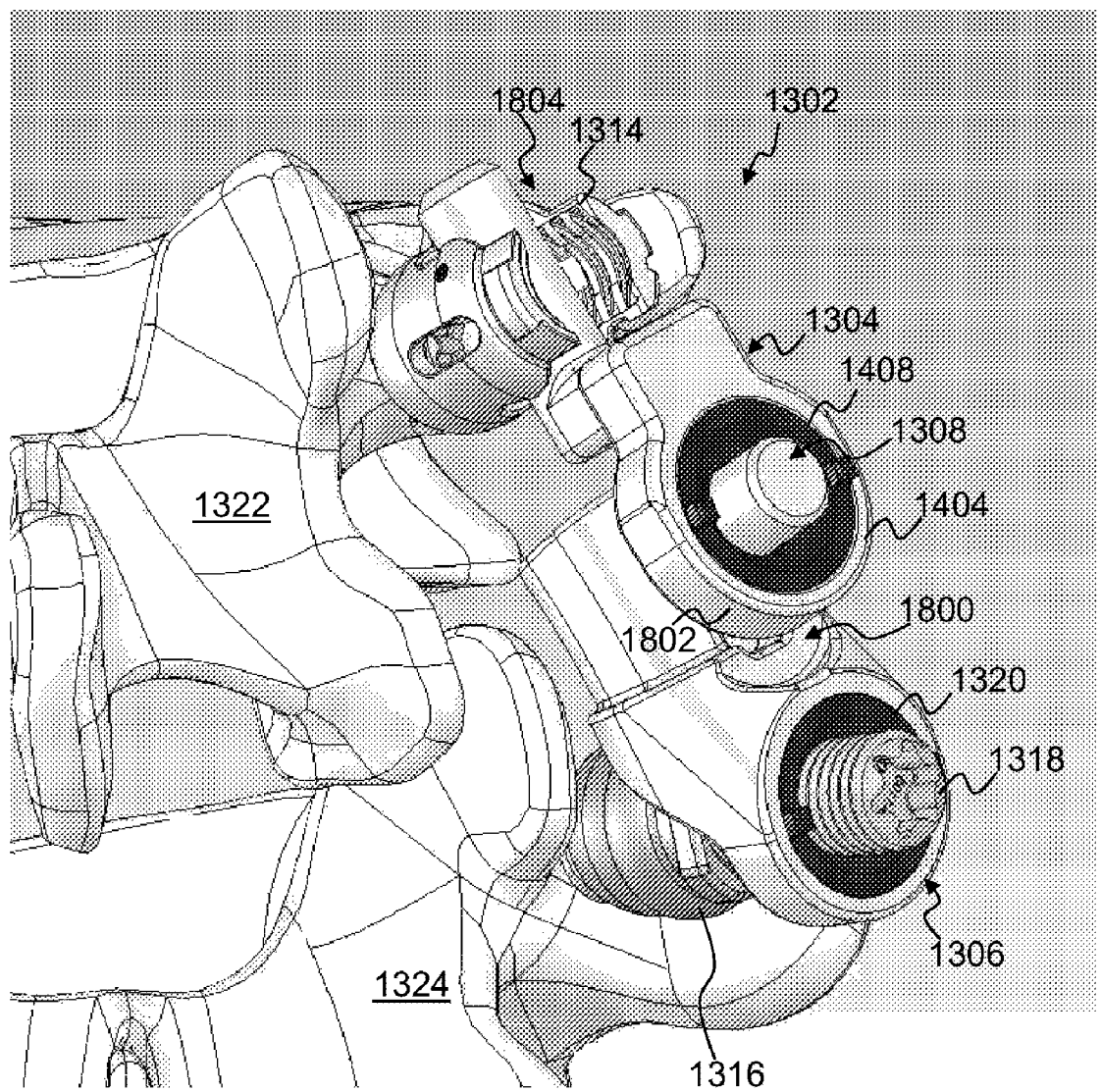
FIG. 18 is a perspective view of one embodiment of the dynamic stabilization system of FIG. 13.

Referring to FIG. 18, a perspective view of one embodiment of the dynamic stabilization device 1302 of FIG. 13 is illustrated. As discussed previously, the sliding member 1308 may move with respect to the anchor member 1306. In the present example, the anchor member 1306 may include an indentation 1800 having a curved profile that substantially matches a curved outer surface 1802 of the dynamic portion 1404 of the anchor member 1304. Accordingly, the anchor member 1304 may move towards the anchor member 1306 until the outer surface 1802 contacts the indentation 1800. It is noted that, due to the substantially similar curves of the outer surface 1802 and indentation 1800, the anchor member 1304 may rotate around the sliding member 1308 even when in contact with the anchor member 1306.

It is understood that the preceding embodiments are for purposes of example only, and that other solutions may be provided. For example, rather than configuring the adjustable anchor portion 1402 to fit and slide with the polyaxial head 1314 prior to being secured with a locking cap, a sliding adjustment between integral components of the dynamic stabilization device 1302 may be provided that can be locked into place during implantation.

Figure 19:
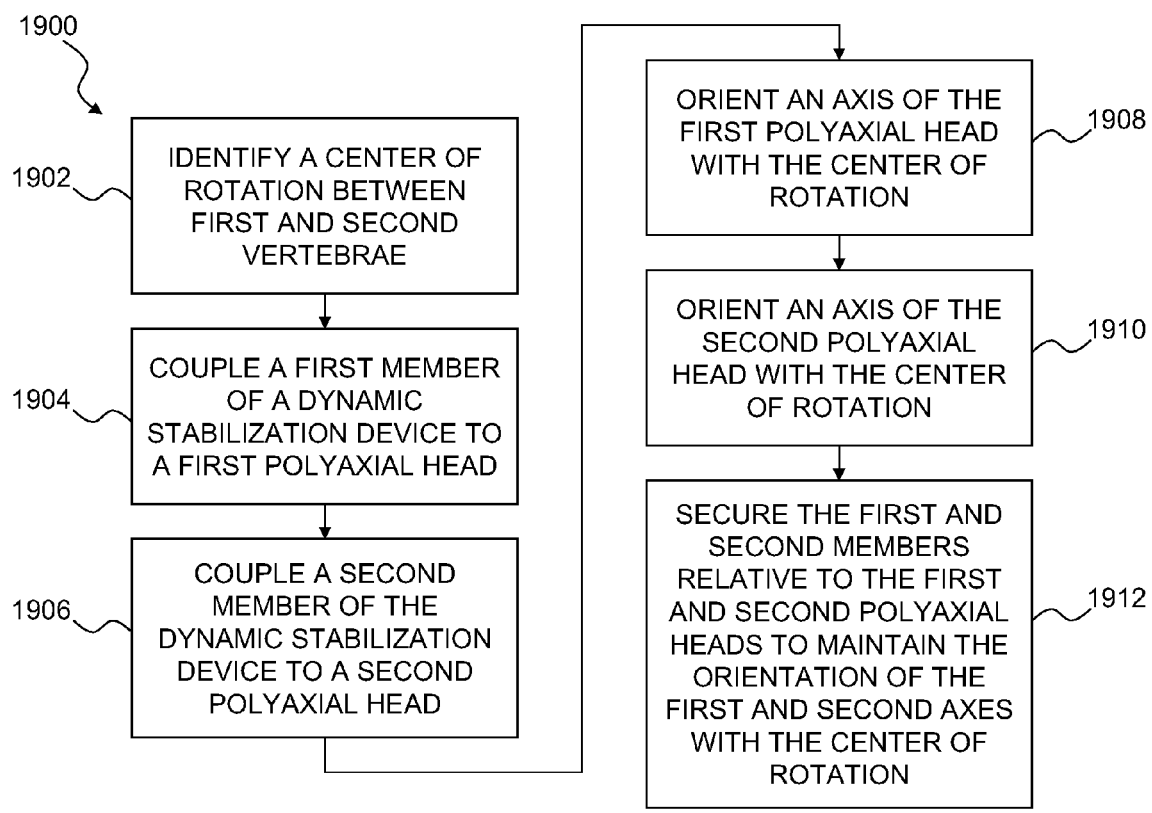
FIG. 19 is a flowchart of one embodiment of a method for using a dynamic stabilization system.

Referring to FIG. 19, in another embodiment, a method 1900 may be used to insert a dynamic stabilization system, such as the dynamic stabilization system 100 of FIG. 1 or 1300 of FIG. 13. In step 1902, a center of rotation may be identified between first and second vertebrae. In step 1904, a first member of a dynamic stabilization device may be coupled to a first polyaxial head and, in step 1906, a second member of the dynamic stabilization device may be coupled to a second polyaxial head. In steps 1908 and 1910, respectively, an axis of each of the first and second polyaxial heads may be oriented with the center of rotation. In step 1912, the first and second members may be secured relative to the first and second polyaxial heads, respectively, to maintain the orientation of the first and second axes with the center of rotation.

In another embodiment, a dynamic stabilization device may be inserted. As illustrated in previous embodiment, the dynamic stabilization device may be designed to be coupled to bone anchors inserted into neighboring vertebrae. For example, the dynamic stabilization device may include a bottom member and a top member that may be coupled together at the proximal ends thereof to allow relative rotation at least about both an axis of roll and a horizontal axis within a range of movement, the range of movement allowing lateral bending and twisting of the upper and lower vertebrae relative to each other while maintaining separation between the vertebrae. The distal end of the bottom member may be coupled to a lower bone anchor and the distal end of the upper member may be coupled to an upper bone anchor. The upper and lower links member be coupled to the bone anchors via a threaded fastener and bushings. The threaded fastener may comprise a bearing post secured by a locking cap or other similar threaded fasteners and locking mechanisms known to those skilled in the art. Both the upper and lower member may be vertically adjusted along the threaded fastener during adjustment of the dynamic stabilization device and thereafter locked down into a substantially permanent position once the device is aligned with the spine's natural center of rotation.

Once the bone anchors and dynamic stabilization device have been implanted and before the implant procedure is completed, the device may be aligned with the spine natural center of rotation. This may be accomplished by several methods, including but not limited to using an aligning cross-connector, using a removable alignment tool that is coupled to the bone anchors, using a removable alignment tool coupled to the dynamic stabilization device between the bone anchors, or various other alignment methods known to those skilled in the art. Generally, the alignment tool may be coupled to the dynamic stabilization device and then an alignment rod may be attached thereto. The alignment rod may be rotated to adjust various components of the dynamic stabilization device such that the components of the dynamic stabilization device align with the spine's natural center of rotation. Alternatively, an alignment tool coupled to the bone anchors may be used to align the bone anchors before any other components of the dynamic stabilization device are implanted.

Although only a few exemplary embodiments of this disclosure have been described in details above, those skilled in the art will readily appreciate that many modifications are possible in the exemplary embodiments without materially departing from the novel teachings and advantages of this disclosure. Also, features illustrated and discussed above with respect to some embodiments can be combined with features illustrated and discussed above with respect to other embodiments. Accordingly, all such modifications are intended to be included within the scope of this disclosure.

What is claimed is:

1. A dynamic stabilization system for attachment to vertebral bodies, said dynamic stabilization system comprising:
   a first bone anchor coupled to a first polyaxial head and a second bone anchor coupled to a second polyaxial head, wherein a first longitudinal centroidal axis passing through a center of said first polyaxial head is aligned with a center of rotation and a second longitudinal centroidal axis passing through a center of said second polyaxial head is aligned with said center of rotation, wherein said center of rotation is within a preselected A-P mark range of said vertebral bodies when said dynamic stabilization system is attached to said vertebral bodies, and wherein said first bone anchor is alignable independently of said first longitudinal centroidal axis and wherein said second bone anchor is alignable independently of said second longitudinal centroidal axis;
   a first member having a first end movably coupled to the said first polyaxial head and a second end; and
   a second member having a third end coupled to said second polyaxial head and a fourth end moveably coupled to said second end, wherein after said dynamic stabilization system is attached to said vertebral bodies said first and second members are configured to maintain the alignment of said first and second longitudinal centroidal axes with said center of rotation during three dimensional movement of said first member relative to said second member.

2. The dynamic stabilization system of claim 1 further comprising a first bearing post coupling said first end and said first polyaxial head, wherein said first bearing post is rotationally coupled to said first end and immovably coupled to said first polyaxial head, and wherein a first longitudinal axis of said first bearing post intersects said center of rotation.

3. The dynamic stabilization system of claim 2 wherein said first bearing post locks a position of said first bone anchor relative to said first polyaxial head.

4. The dynamic stabilization system of claim 2 wherein said third end is immovably coupled to said second polyaxial head.

5. The dynamic stabilization system of claim 2 further comprising a second bearing post coupling said third end and said second polyaxial head, wherein said second bearing post is rotationally coupled to said third end and immovably coupled to said second polyaxial head, wherein a second longitudinal axis of said second bearing post intersects said center of rotation, and wherein said first and second members are configured to maintain said alignment of said first and second longitudinal axes with said center of rotation during three dimensional movement of said first member relative to said second member.

6. The dynamic stabilization system of claim 5 wherein said first bearing post is inserted into a first aperture of said first end and said second bearing post is inserted into a second aperture of said third end.

7. The dynamic stabilization system of claim 6 further comprising first and second bushings inserted into said first and second apertures, respectively, wherein each of said first and second bushings includes a threaded bore configured to engage threads of said first and second bearing posts, respectively, and wherein each of said first and second bushings rotates freely with respect to said first and second apertures, respectively.

8. The dynamic stabilization system of claim 7 further comprising first and second locking caps securing said first and second bearing posts, respectively, to said first and second bushings.

9. The dynamic stabilization system of claim 1 further comprising a pin coupling said first and second members, wherein said pin is inserted into an aperture in each of said second and fourth ends, and wherein said pin forms a pivot point around which said first and second members rotate relative to one another.

10. The dynamic stabilization system of claim 9 wherein said second end includes first and second arms forming a yoke, wherein said fourth end fits between said first and second arms, and wherein said pin extends through said first and second arms.

11. The dynamic stabilization system of claim 1 further comprising a third member coupling said first and second members, wherein said third member has a fifth end movably retained in a cavity in said second end and a sixth end movably retained in a cavity in said fourth end.

12. A dynamic stabilization device for attachment to vertebral bodies comprising:
   a first member having first and second ends, wherein said first end is rotatably coupled to a first polyaxial head about only a first axis that extends through said first end and intersects a center point, wherein said center point is within a preselected A-P mark range of said vertebral bodies when said dynamic stabilization system is attached to said vertebral bodies and wherein said first sol axial head is configured to be head fixedly coupled to a bone anchor;
   a second member having a third end and a fourth end, said third end rotatably coupled to a second polyaxial head about only a second axis that extends through said third end and intersects said center point, and said fourth end moveably coupled to said second end, wherein said second polyaxial head is configured to be fixedly coupled to a bone anchor; and
   a third member movably coupling said second and fourth ends, wherein after said dynamic stabilization system is attached to said vertebral bodies said first, second, and third members are configured to maintain the intersection of said first and second axes with said center point as said center point moves along a curved three dimensional surface during movement of said first member relative to said second member.

13. The dynamic stabilization device of claim 12 wherein said third member is a pin that rotationally couples said first and second members, wherein said pin is received by a first aperture in said second end and a second aperture in said fourth end.

14. The dynamic stabilization device of claim 12 wherein said third member includes a first portion slideably received by a first aperture in said second end and a second portion slideably received by a second aperture in said fourth end.

15. The dynamic stabilization device of claim 14 further comprising a retaining means for retaining at least one of said first and second portions in said first and second apertures, respectively.

16. The dynamic stabilization device of claim 12 wherein said first end includes an aperture configured to receive a bearing post.

17. The dynamic stabilization device of claim 16 further comprising a bearing element retained in said aperture, wherein said bearing element includes a threaded bore configured to engage threads of said bearing post and wherein said bearing element rotates freely with respect to said aperture.

18. The dynamic stabilization device of claim 12 wherein said third end is configured to movably couple to said second polyaxial head.

19. The dynamic stabilization device of claim 12 wherein said first and second members each have a curvature defined to maintain said intersection of said first and second axes with said center point as said center point moves along said curved three dimensional surface.

20. A method comprising:
identifying a center of rotation between first and second vertebrae;
coupling a first member of a dynamic stabilization device to a first polyaxial head;
coupling a second member of said dynamic stabilization device to a second polyaxial head;
orienting an axis of said first polyaxial head with said center of rotation;
orienting an axis of said second polyaxial head with said center of rotation; and
securing said first and second members relative to said first and second polyaxial heads, respectively, to maintain the orientation of said first and second axes with said center of rotation during movement of said first member relative to said second member.

21. The method of claim 20 wherein securing said first member relative to said first polyaxial head includes locking a height of said first member relative to said first polyaxial head.

22. The method of claim 20 further comprising inserting a first bone anchor coupled to said first polyaxial head and inserting a second bone anchor coupled to said second polyaxial head.

23. A dynamic stabilization system for attachment to vertebral bodies, said dynamic stabilization system comprising:
a left construct comprising a left upper polyaxial screw head attaching to an upper vertebra, a left lower polyaxial screw head attaching to a lower vertebra, a left first member connected to said left upper polyaxial screw head, and a left second member connected to said left lower polyaxial screw head, said left first member and said left second member being hingedly connected to each other; and
a right construct comprising a right upper polyaxial screw head attaching to said upper vertebra, a right lower polyaxial screw head attaching to said lower vertebra, a right first member connected to said right upper polyaxial screw head, and a right second member connected to said right lower polyaxial screw head, said right first member and said right second member being hingedly connected to each other;
wherein a first longitudinal centroidal axis passing through a center of said left upper polyaxial head is aligned with a center of rotation, a second longitudinal centroidal axis passing through a center of said left lower polyaxial head is aligned with said center of rotation, a third longitudinal centroidal axis passing through a center of said right upper polyaxial head is aligned with said center of rotation, and a fourth longitudinal centroidal axis passing through a center of said right lower polyaxial head is aligned with said center of rotation;
wherein said left first member and said left second member have a first concave curvature with respect to said vertebral bodies when installed on said vertebral bodies, said first concave curvature defined to maintain said intersection of said first longitudinal centroidal axis and said second longitudinal centroidal axis with said center of rotation; and
wherein said right first member and said right second member have a second concave curvature with respect to said vertebral bodies when installed on said vertebral bodies, said second concave curvature defined to maintain said intersection of said third longitudinal centroidal axis and said fourth longitudinal centroidal axis with said center of rotation.

* * * * *